(12) United States Patent
Zimmermann

(10) Patent No.: US 7,578,917 B2
(45) Date of Patent: Aug. 25, 2009

(54) MAGNETIC LOCKING MECHANISM FOR GEL ELECTROPHORESIS DEVICE

(75) Inventor: Hans-Peter Zimmermann, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 508 days.

(21) Appl. No.: 11/442,513

(22) Filed: May 26, 2006

(65) Prior Publication Data

US 2007/0007140 A1 Jan. 11, 2007

(30) Foreign Application Priority Data

Jul. 7, 2005 (EP) .................................. 05106192

(51) Int. Cl.
*G01N 27/447* (2006.01)
*G01N 27/453* (2006.01)
(52) U.S. Cl. ........................ 204/466; 204/456; 204/616; 204/606
(58) Field of Classification Search ......... 204/600–621, 204/450–470
See application file for complete search history.

(56) References Cited

U.S. PATENT DOCUMENTS

| | | | |
|---|---|---|---|
| 3,798,152 A | 3/1974 | Cawley | 422/82.01 |
| 5,147,522 A | 9/1992 | Sarrine | 204/616 |
| 5,510,081 A | 4/1996 | Edwards et al. | 422/63 |
| 7,276,143 B2* | 10/2007 | Chen | 204/618 |
| 2005/0072678 A1* | 4/2005 | Hunter et al. | 204/601 |

FOREIGN PATENT DOCUMENTS

| | | | |
|---|---|---|---|
| JP | 07-280772 A | * | 10/1995 |
| WO | WO 99/33550 | | 7/1999 |
| WO | WO 00/65336 | | 11/2000 |

OTHER PUBLICATIONS

JPO computer English language translation of Tsutomu et al. JP 07-280772 A, application published on Oct. 27, 1995.*

* cited by examiner

*Primary Examiner*—Alex Noguerola

(57) ABSTRACT

An electrode arrangement for a gel electrophoresis device, the electrode arrangement comprising a first electrode member adapted to provide an electrical contact with one or more gel strips, wherein the first electrode member comprises a first locking element to lock the first electrode member to the gel electrophoresis device.

20 Claims, 17 Drawing Sheets

MAGNETIC LOCKING MECHANISM FOR GEL ELECTROPHORESIS DEVICE

BACKGROUND ART

1. Field of the Invention

The present invention relates to a gel electrophoresis device.

2. Discussion of the Background Art

Electrophoresis is a method to analyze complex mixtures of substances, for instance biological substances like proteins. By electrophoresis, a mixture of different substances may be separated by taking into account the intrinsic charge characteristics of the substances, particularly different isoelectric points of different substances. For an electrophoresis analysis, an analyte may be inserted in a gel strip, and then an electric field is applied along the gel strip so that the electrically charged molecules are separated based on their different electric charges. Along an extension of a gel strip for electrophoresis, a gradient of the local pH value may be generated so that a component having a particular isoelectric point moves along the gel strip and is stopped at a characteristic position and thus pH value of the gel strip, in accordance with the isoelectric point of this component.

U.S. Pat. Nos. 5,989,400, 6,113,766 and 6,599,410 B1 disclose devices for gel electrophoresis.

In conventional gel electrophoresis as described above, substances of an analyte are separated into different fractions which are spatially separated along the extension of the gel strip.

WO 01/86279 A1 and WO 03/019172 A2 disclose an alternative electrophoresis method, wherein a plurality of compartments containing a solution are arranged above a gel strip. After having separated the different fractions of the analyte by applying an electric field, a fraction of substances stopped at a particular position along the gel strip is accumulated in a solution contained in an adjacent one of the plurality of compartments. In comparison to the above-mentioned conventional electrophoresis which may also be denoted as "in-gel electrophoresis" in this specification, the approach of WO 01/86279 A1 and WO 03/019172 A2 may also be denoted as "off-gel electrophoresis" in this specification, since the separated components may be provided off the gel.

SUMMARY OF THE INVENTION

It is an object of the invention to enable improved gel electrophoresis.

According to an exemplary embodiment of the present invention, an electrode arrangement for a gel electrophoresis device is provided, the electrode arrangement comprising a first electrode member adapted to provide an electrical contact with one or more gel strips, wherein the first electrode member comprises a first locking element to lock the first electrode member to the gel electrophoresis device.

According to another exemplary embodiment of the present invention, a gel electrophoresis device is provided, comprising a carrier element (or a support) adapted to receive one or more gel strips, and a counterpart to a first locking element of a first electrode member of an electrode arrangement having the above mentioned features, wherein the counterpart is adapted to lock the first electrode member to the gel electrophoresis device.

According to still another exemplary embodiment of the present invention, a method of operating a gel electrophoresis device having the above mentioned features is provided, the method comprising the steps of receiving, in a carrier element of the gel electrophoresis device, one or more gel strips, and locking an electrode arrangement having the above mentioned features to the gel electrophoresis device.

According to yet another exemplary embodiment of the present invention, a locking system is provided, comprising a magnetic locking element connectable to an electrode member which is adapted to electrically contact one or more gel strips, and a magnetic counterpart connectable to a gel electrophoresis device, wherein the magnetic locking element is adapted to lock the electrode member to the gel electrophoresis device by means of the magnetic counterpart.

In one embodiment, a gel electrophoresis device comprises a platform adapted to receive a carrier element, wherein the carrier element is adapted to receive one or more gel strips. An electrode is adapted to provide an electrical contact with the one or more gel strips, and a magnetic element is adapted to press the carrier element by a magnetic coupling onto the platform. The magnetic element can preferably be embodied into the electrode. Alternatively or in addition thereto, the magnetic element can be embodied into the carrier element, e.g. a permanent magnet or a ferromagnetic element. The magnetic element is preferably embodied into to a lower part of the carrier element, such as the bottom side of the carrier element which faces or is then attached to the platform.

According to an exemplary embodiment of the invention, an electrode arrangement for a gel electrophoresis device is provided comprises a locking element configured to lock the electrode member to the gel electrophoresis device. By providing this locking or fastening element directly on the electrode to be attached to the electrophoresis device, a proper locking of components of the gel electrophoresis device like gel strips, optional compartment frames, insert elements or the like may ensured by simply fastening the electrode member at the gel electrophoresis device, wherein at least a part of the components may be "sandwiched" in between. Thus, a separate fastening element like a fastening plate may be dispensable, since the fastening functionality may be integrated in the electrode member. This may simplify the construction of the gel electrophoresis system and may reduce the number of components.

According to an embodiment of the invention, the locking may be performed in the frame of a modular-type gel electrophoresis device. In other words, as an alternative or in addition to fastening electrodes by a mechanical pressure of a cover of a gel electrophoresis device, the electrodes may be simply clicked on the device so that the locking element provides a secure locking with a locking counterpart of the gel electrophoresis device.

The kind of locking may be of any desired type, for instance magnetically, allowing for a cheap and robust locking. For instance, the electrodes may comprise a small permanent magnet attached thereto, wherein this permanent magnet may lock to a ferromagnetic or permanent magnetic stripe provided on the gel electrophoresis device. Such a stripe may be easy to clean, particularly when such a ferromagnetic stripe is provided at a bottom part of a gel electrophoresis device. The components of the locking system may be shiftable along a gel strip so as to allow for a great degree of flexibility to lock the gel electrophoresis device in accordance with desired geometrical properties.

Since it may be dispensable, according to an embodiment of the invention, to close a cover in order to properly lock the entire system of the gel electrophoresis device, the invention may make it possible to take off a cover in order to inspect an experiment without disturbing the experiment and without disturbing the locking mechanism. However, an electrical voltage applied to gel strips of the gel electrophoresis device may or may not be switched off automatically when opening the cover in order to protect a user from an electric shock.

A stripe of soft iron material may be used as counterpart provided at the gel electrophoresis device. A permanent magnet, for instance made of Neodymium, Samarium-Cobalt or the like may be used as an active magnet forming the magnetic locking element which may be provided at an electrode member.

Using an electromagnet as locking element and/or counterpart may allow for a sufficiently large and attracting pressing force, and may allow to selectively activate (or deactivate) the locking mechanism. Such an electromagnet can be provided at the electrode member and/or on or in a base plate of the gel electrophoresis device.

By using an oblong magnetic strip as magnetic locking element, an electrode slidable along this oblong magnetic strip can be fastened at any desired position over a large range.

One embodiment of the invention may allow to perform a gel strip electrophoresis experiment with magnetically locked electrodes. Electrodes for applying an electric field to gel strips received in the gel electrophoresis device may be provided with a permanent magnet. Ferromagnetic strips which may be arranged beneath a base plate of a gel electrophoresis device may generate a magnet field attracting the permanent magnet, so that the electrodes can be securely locked with the electrophoresis device. The electrodes may be pressed by a magnetic coupling (magnet-stripes) onto the platform. Furthermore, a rail on which the ferromagnetic strip may be provided may simultaneously serve as a high voltage contact rail to provide an electric contact between the electrode and a control circuit for controlling the electrode.

The gel electrophoresis device according to an embodiment of the invention may be used for an "in-gel" electrophoresis analysis and/or for an "off-gel" electrophoresis analysis.

For an electrophoresis analysis using the electrophoresis system according to an exemplary embodiment of the invention, a gel strip may first be hydrated, wherein a pH gradient may be present along an extension of the gel strip as a basis for isoelectric focussing of an analyte to be investigated. One or more of such gel strips may be inserted in corresponding receptions of an insert element. Along the extension of the inserted gel strips, an electric field may be applied to the gel strips individually or concurrently by means of contacting electrode members of the gel electrophoresis device which are brought to a defined electric potential. Such electrode members may be directly electrically coupled to the gel strips or may be dipped in electrolyte containing cavities of compartment frames which may or may not be provided to be brought in functional contact with the gel strips. As a result of the generated electric field, an electric force takes effect on charged components of an analyte in the gel strip. Thus, components of the analyte like proteins are moved along the gel strip. Furthermore, the components to be separated are stopped to remain at respective positions of the gel strip, such positions being defined by the charge properties of the component in combination with the spatially dependent pH gradient of the gel strip.

For an "in-gel" operation mode of the gel electrophoresis device, different fractions of components of the analyte being accumulated at different positions within the gel strip are recovered from the gel strip for instance by cutting a corresponding portion of the gel strip and by dissolving the component located at a particular position in a liquid solution. No compartment frames are necessary for an "in-gel" analysis.

In the context of "in-gel" analysis, the electrode members may be locked to the gel electrophoresis device in such a manner that a gel strip is held in proper (mechanical and thermal) contact with a base plate of the electrophoresis device and is held in proper (mechanical and electrical) contact with electrical contacts of the electrode member.

For an "off-gel" operation mode of the gel electrophoresis device, the carrier element having received gel strips therein, may be provided with compartment frames which may be filled with a liquid. Such compartment frames may be mounted above, below or laterally of the gel strip, however in functional (fluid) connection therewith. The electrodes members may be contacted directly with the gel strip or with electrical contacts provided at (end) portions of the gel strips. Alternatively, the electrode members may contact the compartment frames, particularly electrically conductive liquid contained in cavities of the compartment frames adjacent to (end) portions of the gel strips so as to generate an electric field along an extension of the gel strips. Thus, the gel electrophoresis device may be operated for performing "off-gel" analysis, wherein the general concept of "off-gel" electrophoresis is specified in WO 01/86279 A1 and WO 03/019172 A2.

In the context of "off-gel" analysis, the electrode members may be locked to the gel electrophoresis device in such a manner that a gel strip is held in proper (mechanical and thermal) contact with a base plate of the electrophoresis device and is held in proper (mechanical and electrical) contact with electrical contacts of the electrode member or with the compartment frame which may be located between the electrodes and the gel strip.

Since the electrode arrangement according to an exemplary embodiment of the invention allows for a modular construction of the gel electrophoresis device, it may be adjustably selected whether an "in-gel" experiment, an "off-gel" experiment or a combination of both shall be carried out simultaneously or subsequently.

However, for a proper electrical contact between gel strip and the contacting electrodes, it may be desirable to securely lock the electrodes to the gel electrophoresis device. This may ensure that a constant electric field may be applied to the gel strip or to different compartments of an "off-gel" electrophoresis arrangement.

In the following, exemplary embodiments of the electrode arrangement will be described. However, these embodiments also apply for the gel electrophoresis device, for the method of operating a gel electrophoresis device and for the locking system.

The first locking element may be adapted to removably or detachably lock the first electrode member to the gel electrophoresis device. Thus, after having attached the first electrode member to the gel electrophoresis device, the first electrode member may be detached to remove the locking.

The first locking element may comprise at least one of the group consisting of a magnetic locking element, an electrical locking element, a vacuum locking element, a mechanical locking element, a snap-in locking element, and a hook and loop fastening locking element (Velcro). A magnetic locking element may be manufactured with low costs and may ensure a secure and stable locking between the locking element and a counterpart provided at the gel electrophoresis device. It is also possible to provide an electric locking element, wherein electric potentials of different polarity may be applied to two electrically conducting (and optionally isolated) components of the electrode arrangement on the one hand and of the gel electrophoresis device on the other hand. Consequently, an attracting and properly controllable electric field may be generated between the two electrically conducting components, thus allowing to provide a secure locking between electrode arrangement and gel electrophoresis device. A vacuum locking element may generate an attracting force by means of a low pressure, so that the two components (electrode and gel electrophoresis device) may be held together by means of a vacuum. Such a vacuum locking element may also be easily controllable and selectively releasable by removing the vacuum. A mechanical locking element like a screw and thread connection, a snap-in connection or an adhering surface may further be used for locking the electrode to the gel electrophoresis device with low effort.

The first locking element may be adapted to lock the first electrode member to a temperature-controllable carrier element of the gel electrophoresis device. According to this embodiment, the temperature of gel strips received in such a carrier element may be controlled. This may be advantageous or necessary in order to avoid that the ohmic losses due to the electric field applied to the gel strip heat the sample or the analyte to a temperature at which their components may be damaged. For instance, proteins tend to denature above a particular temperature. In another scenario, it may be advantageous to heat the sample contained in the gel, for instance to decrease the time needed for the electrophoresis analysis. However, heating or cooling the gel strip requires a proper thermal coupling between the gel electrophoresis device having heating or cooling elements (for instance heating coils or a Peltier cooling device) and the gel strips, so that a proper locking of the electrodes to the gel electrophoresis device via the gel strips may promote a proper thermal coupling.

Furthermore, the electrode arrangement may comprise a second electrode member adapted to provide an electrical contact with one or more gel strips. The second electrode member may comprise a second locking element to lock the second electrode member to the gel electrophoresis device. By means of a second electrode member having a second locking element, a second portion of the gel strip may be locked so that the stability of the system may be further improved.

The electrode arrangement may comprise a first housing in which the first electrode member may be arranged. Furthermore, the electrode arrangement may comprise a second housing in which the second electrode member is arranged. The first housing may be provided as a component which is separated from the second housing, so that the two electrode members may be independently attached to the gel electrophoresis device, thus increasing the flexibility and the modular character of the system. For instance, such a flexibility may be increased since the first and/or the second electrode member may be positioned and locked to the gel electrophoresis device at variable distance from another, for instance to meet requirements of pre-given length of the gel strips.

The first locking element and/or the second locking element may comprise at least one of the group consisting of a permanent magnet, an electromagnet, and an electric field generating component. These embodiments relate to a magnetic or electric locking between electrode members and gel electrophoresis device and may be combined or substituted by the above-mentioned or other alternatives.

The first locking element and/or the second locking element may be arranged at a lateral portion of the first housing and/or of the second housing. Thus, the locking mechanism may be positioned at a lateral end portion of the locking elements leaving a central portion of the electrode arrangement free from locking elements. For instance, the electrode members may be realized in an essentially U-shaped manner, wherein the locking mechanism may be localized at outer portions of the parallel portions of the U-shaped electrode members.

The first electrode member and/or the second electrode member may comprise an electric contact for supplying an electric signal to the first electrode member and/or to the second electrode member, wherein the electric contact may be provided at a lateral portion of the first housing and/or of the second housing. In other words, additionally or alternatively to the lateral arrangement of the locking elements, an electrical contact of the electrode members may also be provided laterally. Thus, a proper locking of the electrode arrangement to the gel electrophoresis device may simultaneously allow for a secure electric contact between the electrodes and their electrical counterparts. Mechanical and electrical stability may be achieved simultaneously by taking this measure.

In the following, further exemplary embodiments of the gel electrophoresis device will be described. However, these embodiments also apply for the electrode arrangement, for the method of operating a gel electrophoresis device and for the locking system.

The gel electrophoresis device may be adapted for fluid separation by means of an applied electric field. More particularly, gel strips may be inserted in the carrier element, the first electrode member may be locked to the counterpart of the gel electrophoresis device, and then an electric field may be applied to the gel strips by means of the first electrode member, and optionally by a second electrode member. In the presence of such an electric field, an analyte contained in the gel strip may be separated in a plurality of different components, for instance via isoelectric focusing.

The gel electrophoresis device according to an embodiment of the invention may comprise an electrode arrangement having the above-mentioned features.

Particularly, the counterpart to the first locking element of the first electrode member may comprise at least one of the group consisting of a magnetic counterpart, an electric counterpart, a vacuum counterpart, a mechanical counterpart, a snap-in counterpart, and a hook and loop fastening counterpart. Thus, the fastening type of the counterpart is correlated to the fastening type of the first locking element. For instance, in the case of a hook and loop fastening connection, one of the first locking element and the counterpart comprises hooks, and the other one comprises loops. Or, for a magnetic connection, both counterparts comprise magnetic material which functions together to generate an attracting magnetic force.

The counterpart may comprise at least one of the group consisting of a permanent magnet, an electromagnet and an electric field generating component.

The carrier element may be temperature-controllable. In other words, a temperature control unit may be integrated in the carrier element for selectively heating or cooling the gel strips. More generally, control or regulation components may be provided in the gel electrophoresis device for adjusting a temperature of the gel strips. Thus, the temperature may be introduced as a variable parameter in the gel electrophoresis experiment.

The counterpart of the gel electrophoresis device may comprise one or more electric and/or magnetic field generating strips provided essentially parallel to the one or more gel strip so that the first electrode member and/or the second electrode member is or are shiftable along the one or more electric and/or magnetic field generating strips. A sliding direction for moving the electrode members along the extension of the gel strips may be defined by means of a magnetic field generating strip or an electric field generating strip (for instance made of a ferroelectric material or brought to a predetermined electrical potential), so that, when a user shifts the electrode members along the gel strips, the attracting electric or magnetic force between the electric or magnetic field generating strips and the electric or magnetic locking elements of the electrode members may serve as a mechanical guide.

Particularly, at least one rail may be provided essentially parallel to the one or more gel strips so that the first electrode member and/or the second electrode member may be shiftable along the at least one rail. Such a rail may be designed as a bar or a track along which the counterpart strip may be guided.

More particularly, the counterpart may be arranged along the at least one rail, for instance along a bottom of the at least one rail. By positioning the counterpart at an underside of the rail, the counterpart is hidden and may be less prone to be polluted, since it is shielded from dirt or other impurities.

Additionally or alternatively, an electric contact for supplying an electric signal to the first electrode member and/or to the second electrode member may be arranged along the at least one rail or along a top of the at least one rail. By providing an electrical contact, particularly for supplying a high voltage signal, along an upper side of the rail, a sliding of the electrode members along the rail continuously ensures a proper connection or locking, and does also provide a proper electrical connection.

Furthermore, the gel electrophoresis device may comprise one or more insert element receptions, wherein each of the one or more insert element receptions may be adapted to removably receive an insert element forming the carrier element. Thus, a plurality of insert elements each capable of receiving one or more gel strips may be flexibly and removably attached to the gel electrophoresis device. It may also be possible to removably attach to the insert element, for example above the gel strip receptions, compartment frames so as to allow both, an "in-gel" electrophoresis experiment and/or an "off-gel" electrophoresis experiment.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION OF THE PREFERRED EMBODIMENT

Figure 1:
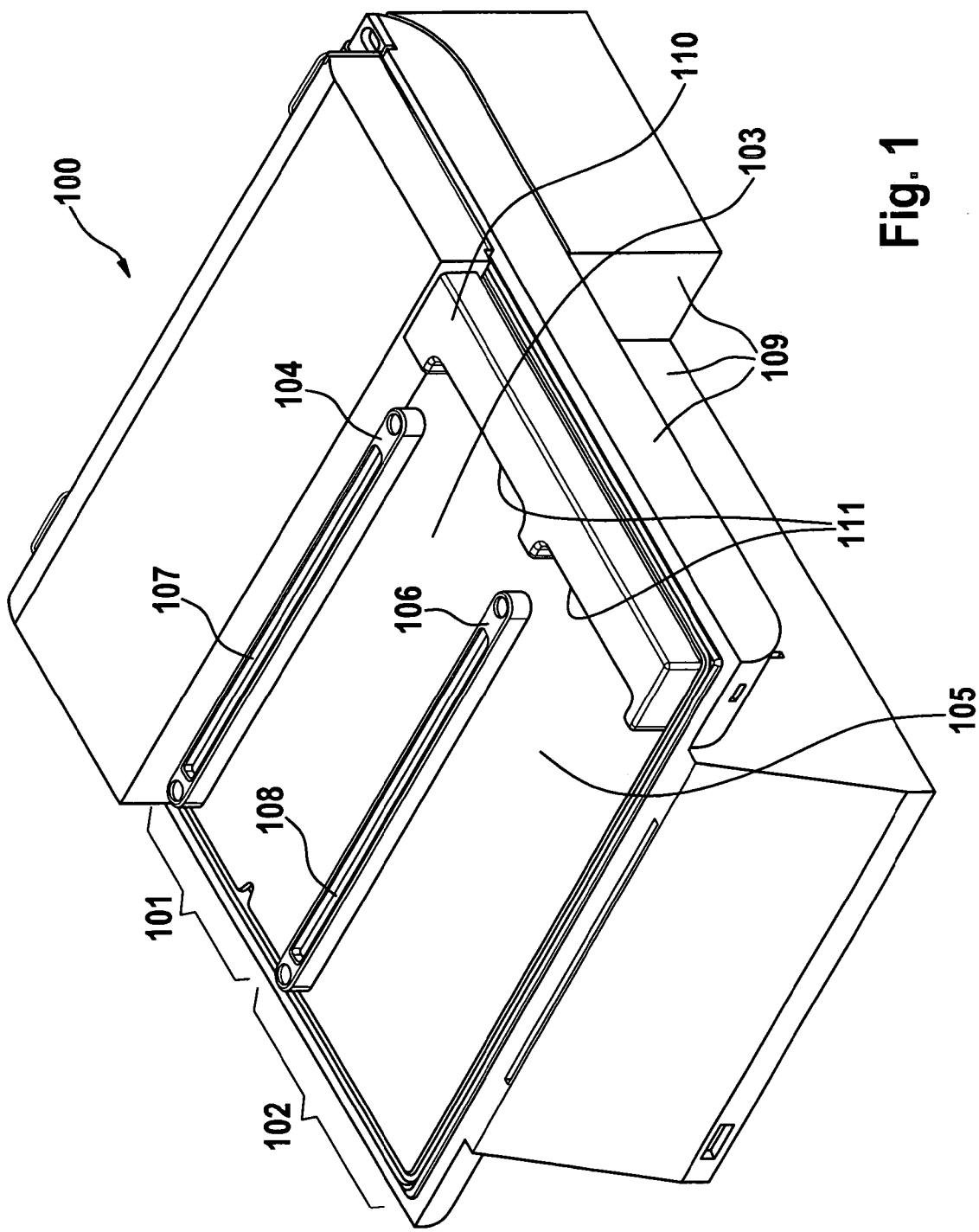
FIG. 1 is a three-dimensional view of a gel electrophoresis device according to an exemplary embodiment of the invention in a partially disassembled state.

The illustration in the drawing is schematically.

In the following, referring to FIG. 1, a gel electrophoresis device 100 according to an exemplary embodiment of the invention will be described.

In FIG. 1, the gel electrophoresis device 100 is illustrated without a cover plate or cap which may be put on the top of the gel electrophoresis device 100 to cover the elements 101 to 108, 110, 111. Such a cover may be opened for mounting components of the modular gel electrophoresis device 100 in order to prepare a gel electrophoresis analysis in a user-defined manner. During the actual gel electrophoresis analysis, the cover may be closed in order to avoid undesired influences of the external environment on the gel electrophoresis analysis and to optionally improve a locking or fastening of the modular components received in the interior of the gel electrophoresis device 100.

Particularly, such a cover can be positioned on the top of the device 100 in order to cover a first insert element reception 101 and a second insert element reception 102. The first insert element reception 101 which is adapted to receive an insert element or a tray for performing a user-defined gel electrophoresis analysis comprises a planar platform 103 and a bar-like rail 104. In a similar manner, the second insert element reception 102 comprises a planar platform 105 and a bar-like rail 106.

The platforms 103 and 105 are, independently from each other, temperature-controllable, that is to say heatable or coolable, in order to selectively heat or cool a sample to a selectable temperature. A heating element (not shown) integrated within the platforms 103, 105 may comprise a heating coil or a heating spiral which may be controlled either by the gel electrophoresis device 100 automatically, or in a user-defined manner via a user interface, for instance a graphical user interface. A cooling element (not shown) integrated within the platforms 103, 105 may comprise a Peltier cooling device or a water cooling which may be controlled either by the gel electrophoresis device 100 automatically, or in a user-defined manner via the user interface.

For performing an electrophoresis experiment it might be appropriate to apply electrical signals (for instance an electrical potential) to electrodes which may be removably attached to the gel electrophoresis device 100, as will be described in detail below. For this purpose, a first electrode member may be connected to a strip-like first electrical contact 107 or 108 which is provided at each of the rails 104, 106. Essentially parallel to the strip-like first electrical contact 107, 108, at a bottom side of each of the rails 104, 106, a ferromagnetic strip (not shown in FIG. 1, see FIG. 16) is arranged which may allow to lock the electrode members to the gel electrophoresis device 100, for instance in order to fasten gel strips used for a gel electrophoresis experiment to the gel electrophoresis device 100.

Furthermore, the gel electrophoresis device 100 comprises a casing 109, wherein a plurality of further functional components (for instance electric circuits, etc.) of the gel electrophoresis device 100 which are not shown in FIG. 1 are housed in the interior of the casing 109. FIG. 1 shows a disassembled operation state of the gel electrophoresis device 100 without any insert element mounted on the insert element receptions 101, 102.

Figure 2:
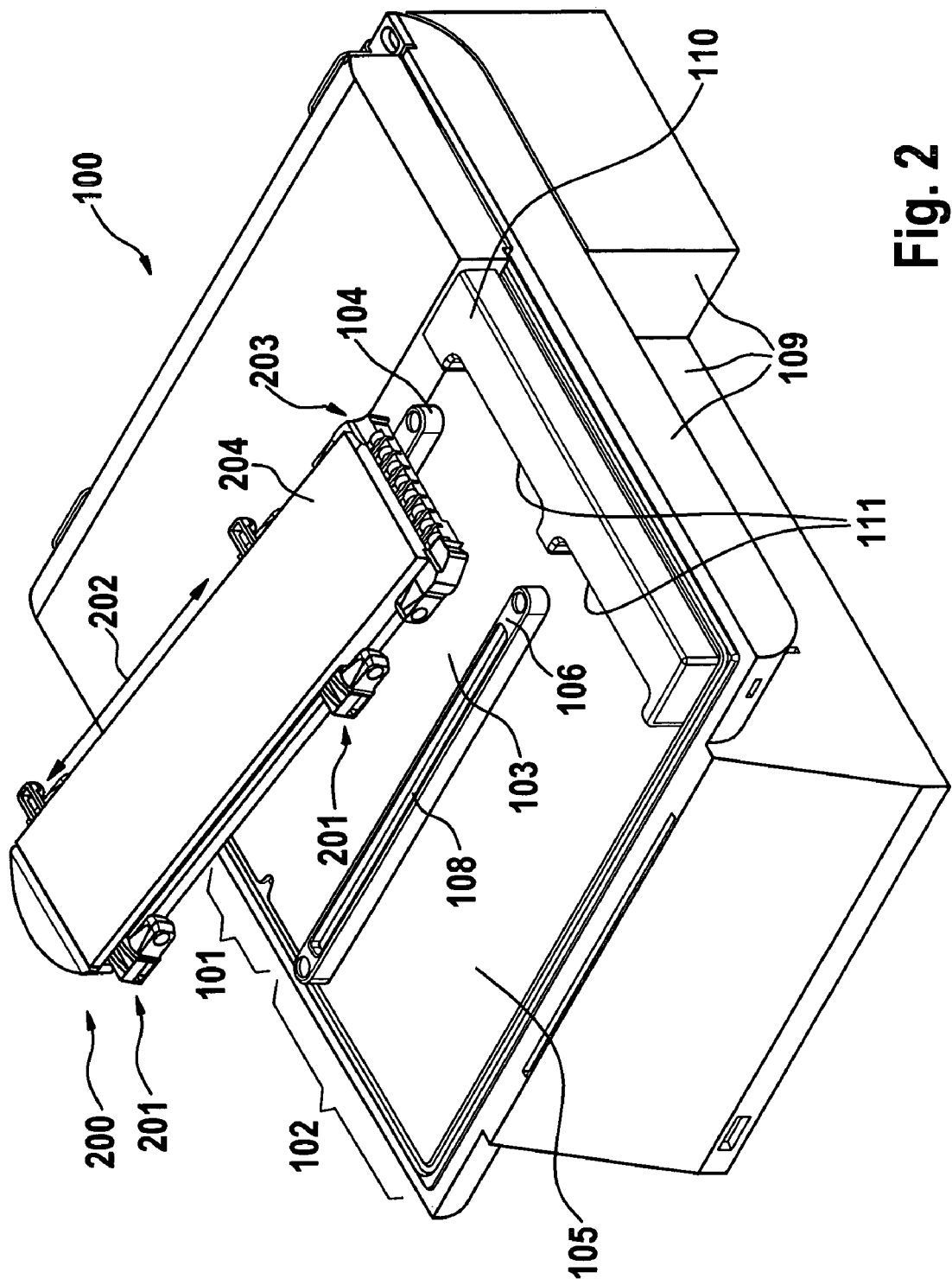
FIG. 2 is a three-dimensional view of the gel electrophoresis device of FIG. 1 with an insert element according to an exemplary embodiment of the invention partially mounted to the gel electrophoresis device.

FIG. 2 shows the gel electrophoresis device 100 in an operation state in which an insert element 200, which may also be denoted as a tray, is inserted in the first insert element reception 101. The insert element receptions 101, 102 are spatially defined by the platforms 103, 105, by the positions and the design of the rails 104, 106, and also by a boundary member 110 which has specially-shaped recesses 111 geometrically adapted to the shape of an end portion of the insert element 200.

As can be seen in FIG. 2, the insert element 200 comprises a first electrode member 201 which is shown twice in FIG. 2 to illustrate that the first electrode member 201 is provided slidably along a sliding direction 202. Furthermore, the insert element 200 comprises a second electrode member 203 which is provided in a fixed manner, that is to say in a manner as to be not slidably. However, in an alternative embodiment, also the second electrode member 203 may be provided slidably along the sliding direction 202. The construction and the function of the electrode members 201, 203 will be described in more detail below.

Furthermore, the insert element 200 comprises a cover plate 204 which can be mounted on the top of the modularly designed insert element 200 after having inserted a plurality of elements in the interior of the insert element 200. Such a cover 204 may have the function of fastening and protecting the elements located in the interior of the insert element 200.

As can be seen in FIG. 2, the already preconfigured and premounted insert element 200 can be inserted as a whole in one of the insert element receptions 101, 102. Alternatively, only a carrier element of the insert element 200 may be inserted in a desired one of the insert element receptions 101, 102, and the experimental components can then be mounted in such a carrier element in an operation state of the carrier element in which it is received in one of the insert element receptions 101, 102. Although two insert element receptions 101, 102 are shown in FIG. 2, it is possible to use more or less insert elements 200 and insert element reception 101, 102, and to insert one or at least three insert elements 200 in the insert element receptions 101, 102.

Figure 3:
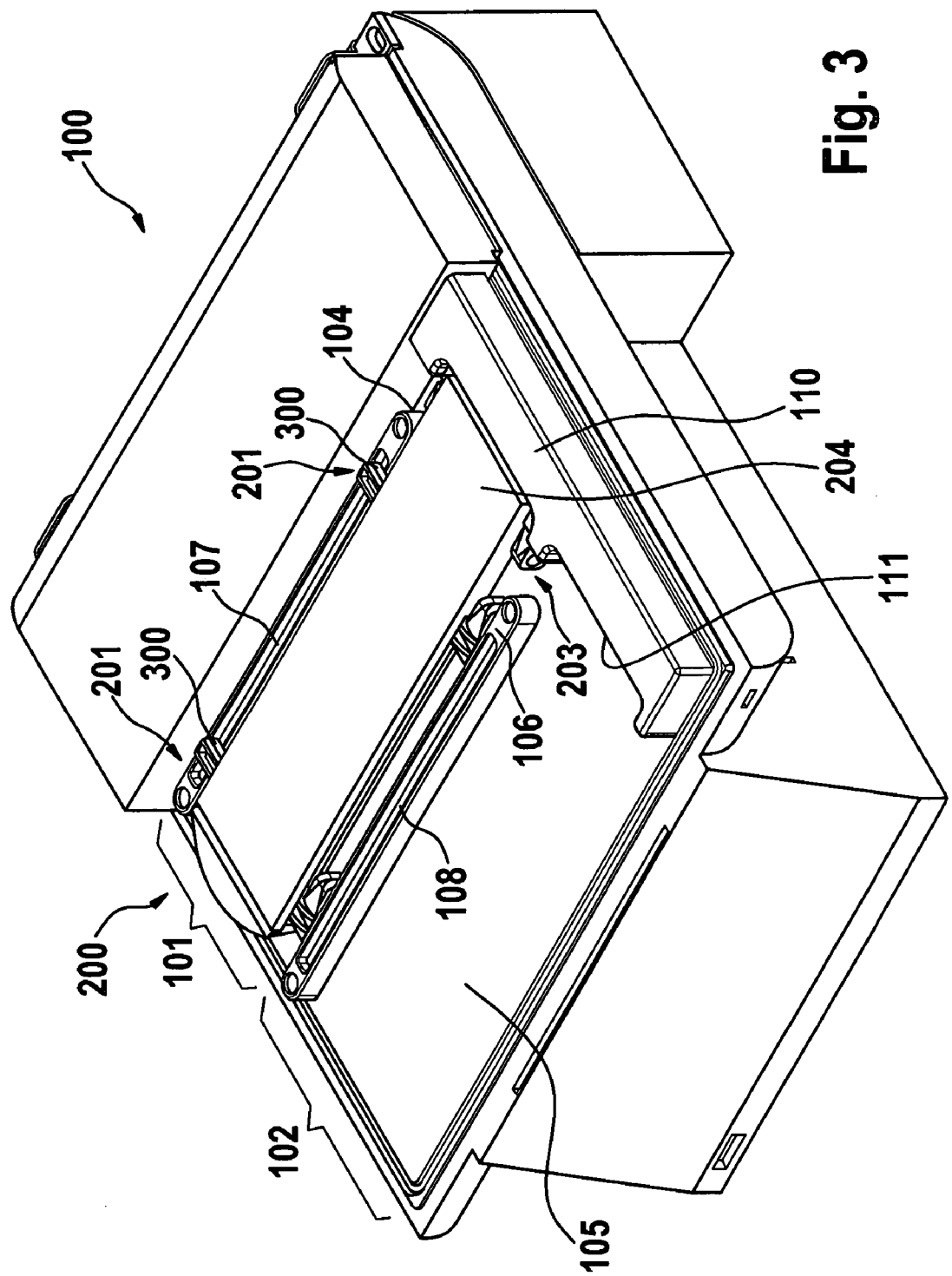
FIG. 3 is a three-dimensional view of the gel electrophoresis device of FIG. 1 with the insert element of FIG. 2 mounted thereon.

FIG. 3 shows the gel electrophoresis device 100 in a further operation state in which the insert element 200 is readily and completely inserted in the insert element reception 101.

In this operation state, the first electrode member 201 which is, also in FIG. 3, shown twice, has a contact element 300 which is mechanically and electrically coupled to the strip-like first electrical contact of the rail 104. As will be described in more detail below, apart from this electrical contact between the components 300, 107, a magnetic locking mechanism is provided by the interaction between a permanent magnet provided at a lateral position of the first electrode 201 in vicinity of the contact element 300 and a strip made of a magnetic material which is provided at a bottom side of the rail 104 and extending parallel to the electrical contact 107 of the rail 104.

Figure 4:
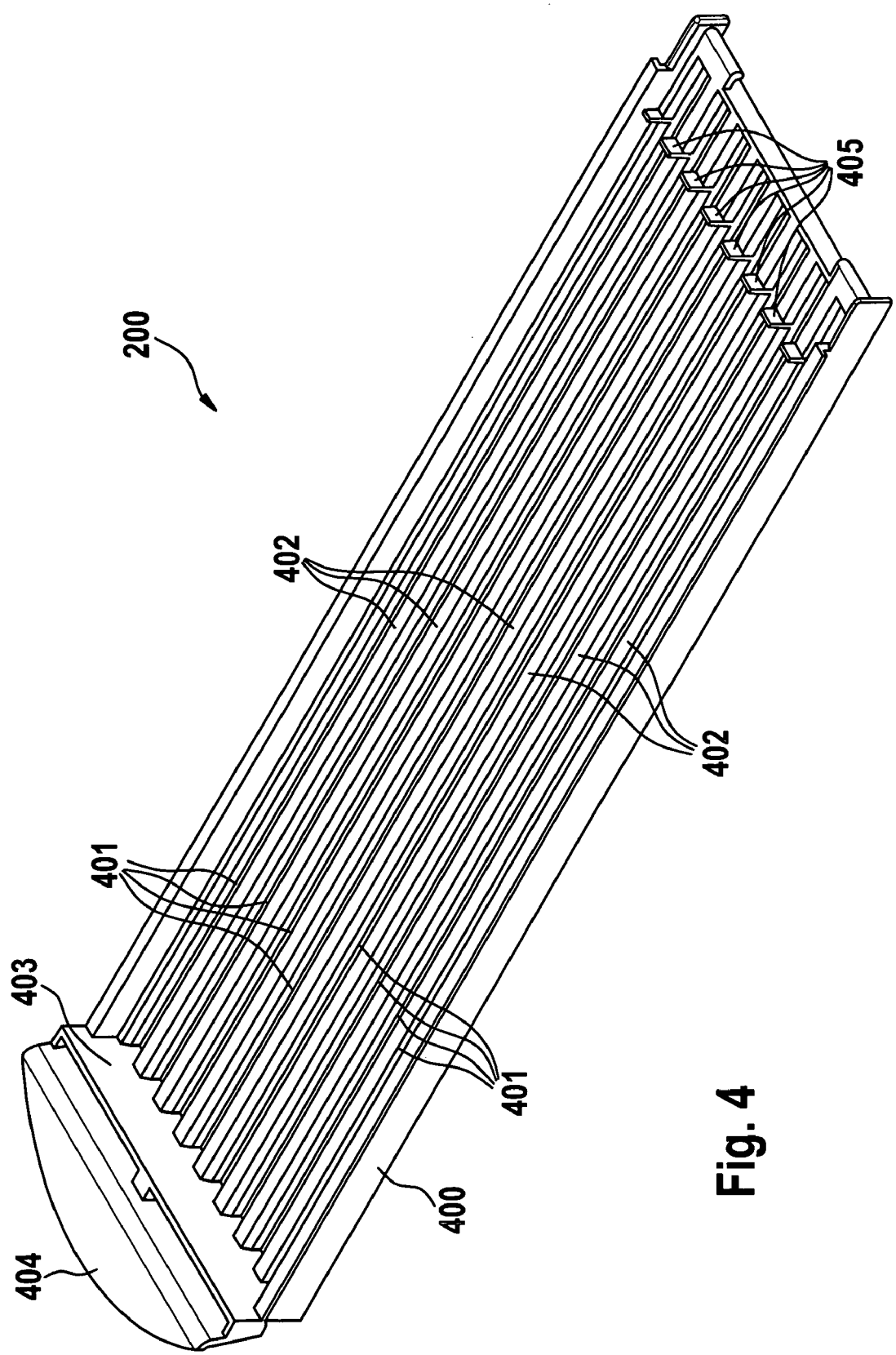
FIG. 4 is a three-dimensional view of the insert element of FIG. 2 in a disassembled state.

In the following, referring to FIG. 4, the insert element 200 shown in FIG. 2 is shown in a disassembled state without cover 204 and will be described in detail in the following.

The insert element 200 for the gel electrophoresis device 100 comprises a carrier element 400 comprising a plurality of channel-like gel strip receptions 401. Each of the gel strip receptions 401 is adapted to receive a strip-like gel strip therein. Furthermore, each of the gel strip receptions 401 is further adapted to receive a compartment frame (see FIG. 6) in such a manner that the corresponding compartment frame is located closely, in the embodiment of FIG. 4 above, the corresponding gel strip. Any of the gel strip receptions 401 is adapted to removably and substitutably receive a corresponding gel strip, so that a gel strip may be inserted in each of the gel strip receptions 401 in accordance with requirements of a particular experiment or analysis. It is possible to remove a gel strip after use and replace it by a new gel strip for a subsequent experiment or analysis. Beyond this, each of the gel strip receptions 401 may removably receive a compartment frame to be located above the gel strip.

Each of the gel strip receptions 401 is designed as an essentially rectangular groove for receiving an oblong bandlike or bar-like gel strip. Above this groove, rib-like or tapered sidewalls 402 are provided to receive compartment frames in a manner as to contact the gel strip below. The compartment frames may be fastened by press-fit between two adjacent ribs 402.

At a first end portion of the insert element 200, an essentially vertical border wall 403 is provided which may abut to an end portion of compartment frames or gel strips inserted above or in the gel strip receptions 401. Close to the wall 403, a grip 404 is provided to allow a user to hold and operate the insert element 200 in a convenient manner. At a second end portion of the insert element 200, individual vertical wall elements 405 are provided opposing the vertical wall 403 so that inserting the compartment frames can be mechanically supported by means of the vertical border elements 405 which may receive a compartment frame in a snap-fit manner.

The insert element 200 may be integrally formed and may be manufactured, for instance, as an injection molded element. According to the described embodiment, the insert element 200 may be made of a plastics material.

The insert element 200 has a thin-walled bottom, that is to say a thin-wall base within the grooves forming the gel strip receptions 401. Optionally, a material for supporting or promoting a thermal contact between the heating/cooling elements provided in the platforms 103, 105 on the one hand and gel strips inserted in the gel strip receptions 401 on the other hand may be provided at the base within the grooves forming the gel strip receptions 401. For example, a metallic material, mineral fibers or a ceramics may be embedded in this bottom, or the bottom may be manufactured of one of these materials.

Figure 5:
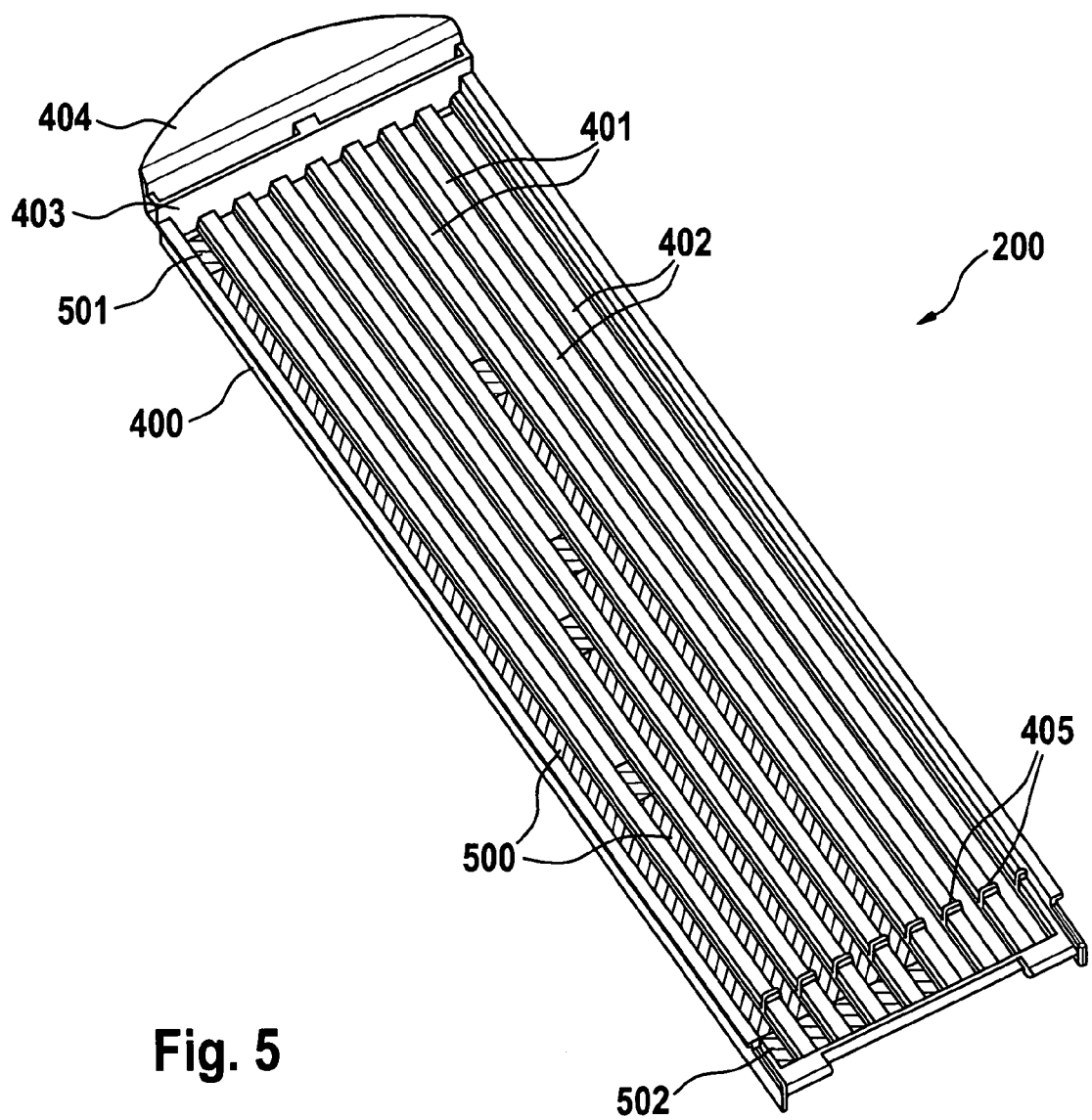
FIG. 5 is a three-dimensional view of the insert element of FIG. 4 with gel strips mounted therein.

FIG. 5 shows the insert element 200 in an operation state in which a plurality of gel strips 500 have been inserted in some of the gel strip receptions 401. However, some of the gel strip receptions 401 may remain free of gel strips 500.

As can further be seen, each of the gel strips 500 comprises a first contact 501 at a first end portion thereof, and comprises a second contact 502 at a second end portion of the corresponding gel strip 500. These contacts 501, 502 may be contacted by electrode members 201, 203, respectively, in order to apply an electric field along the extension of the respective gel strip 500. A central (major) part of the gel strips 500 is formed by gel material, wherein a pH gradient may be generated along the extension direction of the gel strip 500 in order to allow a separation of components of an analyte by means of isoelectric focussing. Furthermore, before using the gel strips, the gel strips may be hydrated, after being inserted in the gel strip receptions 401 or before being inserted in the gel strip receptions 401, for instance in a biolab. The gel material may be provided on a strip-like plastics substrate of the gel strip 500.

As can be seen in FIG. 5, gel strips 500 of different lengths may be inserted in the gel strip receptions 401 in accordance with the modular character of the electrophoresis system according to an embodiment of the invention.

When an analyte is inserted in the gel strips 500, for instance by injecting the analyte by means of a pipette or the like, different fractions of molecules (for instance proteins) of the analyte having different charge properties are moved with different velocities along the gel strips 500 until they are stopped at a particular position of the gel strip 500, which is defined by the local pH gradient at this position and the charge of the corresponding molecules. Thus, different substances may be separated to form individual bands along the extension of the gel strips 500.

Thus, FIG. 5 shows a configuration of the insert element 200 for a so-called "in-gel electrophoresis experiment", that is to say a gel electrophoresis experiment in which different fractions of substances of an analyte inserted in the gel strip 500 are separated so that different bands of fractions are stopped at different positions within the gel strips 500. For recovering the separated components, the corresponding gel strip 500 may be cut, or the respective fractions may be dissolved from the gel strip 500, for instance by means of a pipette.

In the following, referring to FIG. 6, an alternative operation state or configuration state of the insert element 200 will be described so that the insert element 200 in the configuration of FIG. 6 can be used for so-called "off-gel electrophoresis" in accordance with the general concept disclosed, for instance, in WO 01/86279 A1 and WO 03/019172 A2.

Figure 6:
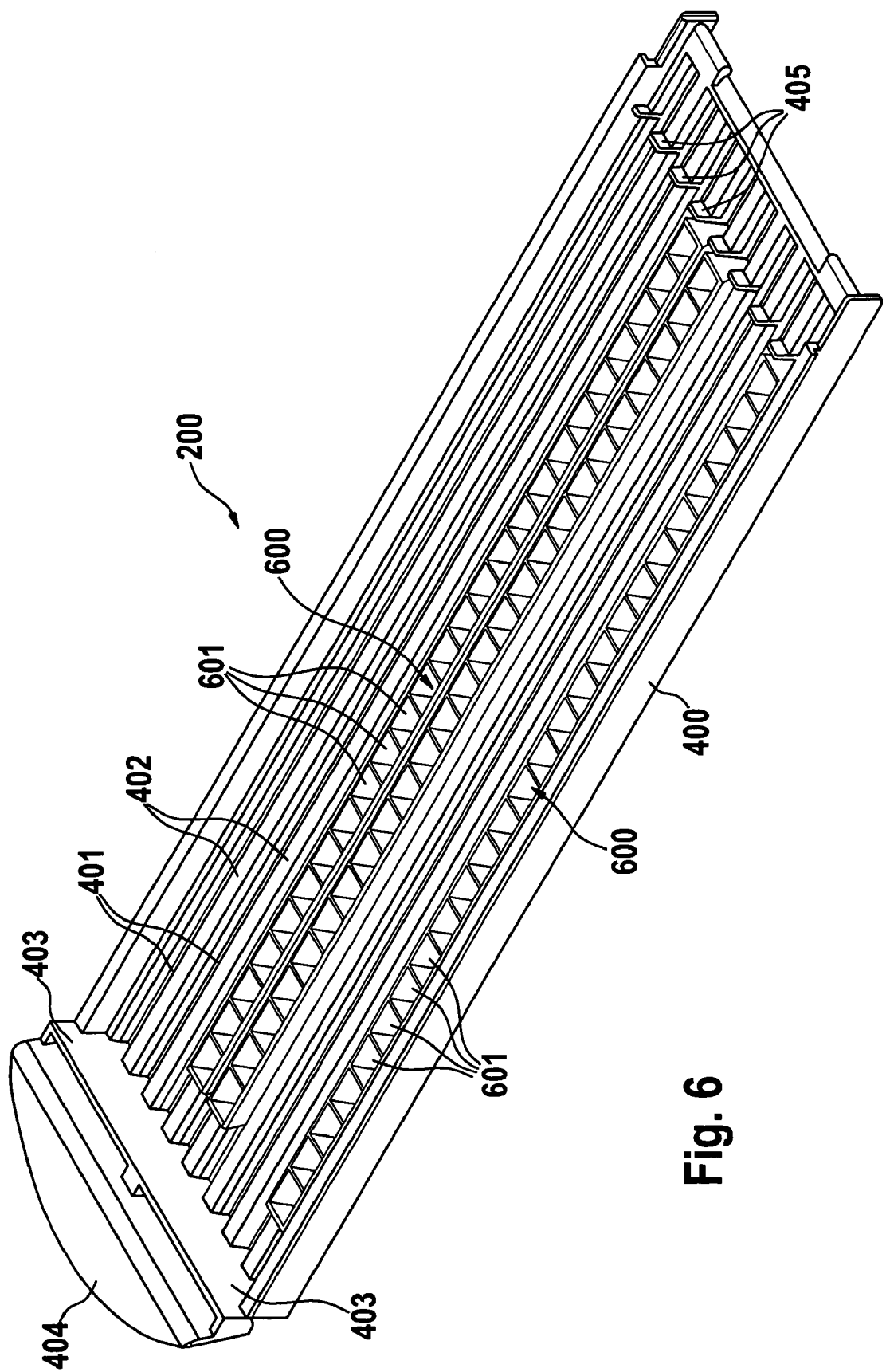
FIG. 6 is a three-dimensional view of the insert element of FIG. 4 with compartment frames mounted on some of the gel strips.

In the configuration shown in FIG. 6, a plurality of compartment frames 600 are inserted in some of the receptions defined as portions between adjacent ribs 402. Before inserting the compartment frames 600 into the corresponding grooves, the grooves are equipped with gel strips (not shown in FIG. 6) inserted in the corresponding gel strip receptions 401.

The compartment frames 601 may then be positioned above the gel strips 500. Each of the compartment flames 600 comprises a plurality of cavities 601 each of which may be filled individually with analyte, buffer, electrolyte, or any other solution. The cavities 601 may be arranged in a one-dimensional manner, that is to say in a row-like manner. The cavities 601 may be filled, for instance, by means of a pipette. Within a cavity 601, there may be a direct functional connection between fluid inserted in the cavity 601 and the adjacent gel part of the gel strip 500 below the respective cavity 601. Thus, the compartment frames 600 are adapted for providing an analyte filled compartment fluid coupled to the gel strip 500.

In the following, a principle of an "off-gel electrophoresis" experiment will be described which may be performed with the configuration of FIG. 6.

For this purpose, gel strips 500 may be used.

First, a gel strip 500 is hydrated and is inserted in one of the gel strip receptions 401. Then, a corresponding compartment frame 600 is positioned above the respective gel strip 500 received in the gel strip reception 401 and abuts laterally against sidewalls of the ribs 402. One or both end portions of the compartment frames 600 may also be fixed by means of the vertical wall elements 403, 405. At an open bottom part of the compartment frame 600, it abuts against an upper side of the gel strip 500 so as to enable fluid communication between the gel and fluid contained in the cavities 601 of the compartment frame 600.

Electrode members 201, 203 may be electrically connected to contacts 501, 502 of the gel strip 500. Alternatively, electrical contacts of the electrode members 201, 203 may be directly "dipped" in cavities 601 of the compartment frames 600 so as to apply an electric field along an extension of the gel strip 500.

An analyte may be filled in one or more of the cavities 601, for instance in one of the cavities located at one of the end portions of the compartment frames 600. The analyte may then flow (for instance promoted by effects like diffusion) into the gel strip 500 below the respective cavity 601. As a consequence of an applied electric field, charged substances of the analyte may then be moved along an extension of the gel strip 500. Due to the isoelectric focusing occurring in accordance with the pH gradient provided along the gel strip 500, each fraction of substances stops at a particular position of the gel strip 500. The fraction or component may then flow (for instance promoted by effects like diffusion) from the particular position within the gel strip 500 back to the respective cavity 601 above this position. This cavity 601 may be filled with a buffer solution, so that the corresponding fraction is accumulated in a particular one of the cavities 601 and can be recovered by receiving the substance comprising buffer in the cavity 601, for instance by means of a pipette.

Coming back to FIG. 1, the gel electrophoresis device 100 having the insert element receptions 101, 102 is adapted so that the insert element 200 may be inserted in a corresponding one of the insert element receptions. Then, also with assistance of the electrical contacts 107, 108, which may be brought in contact with electrical contacts of the electrode members 201, 203, an electric field may be applied along an extension of the gel strips 500 by means of an applied electric field due to the electrical contacting of the gel strips 500.

Figure 7:
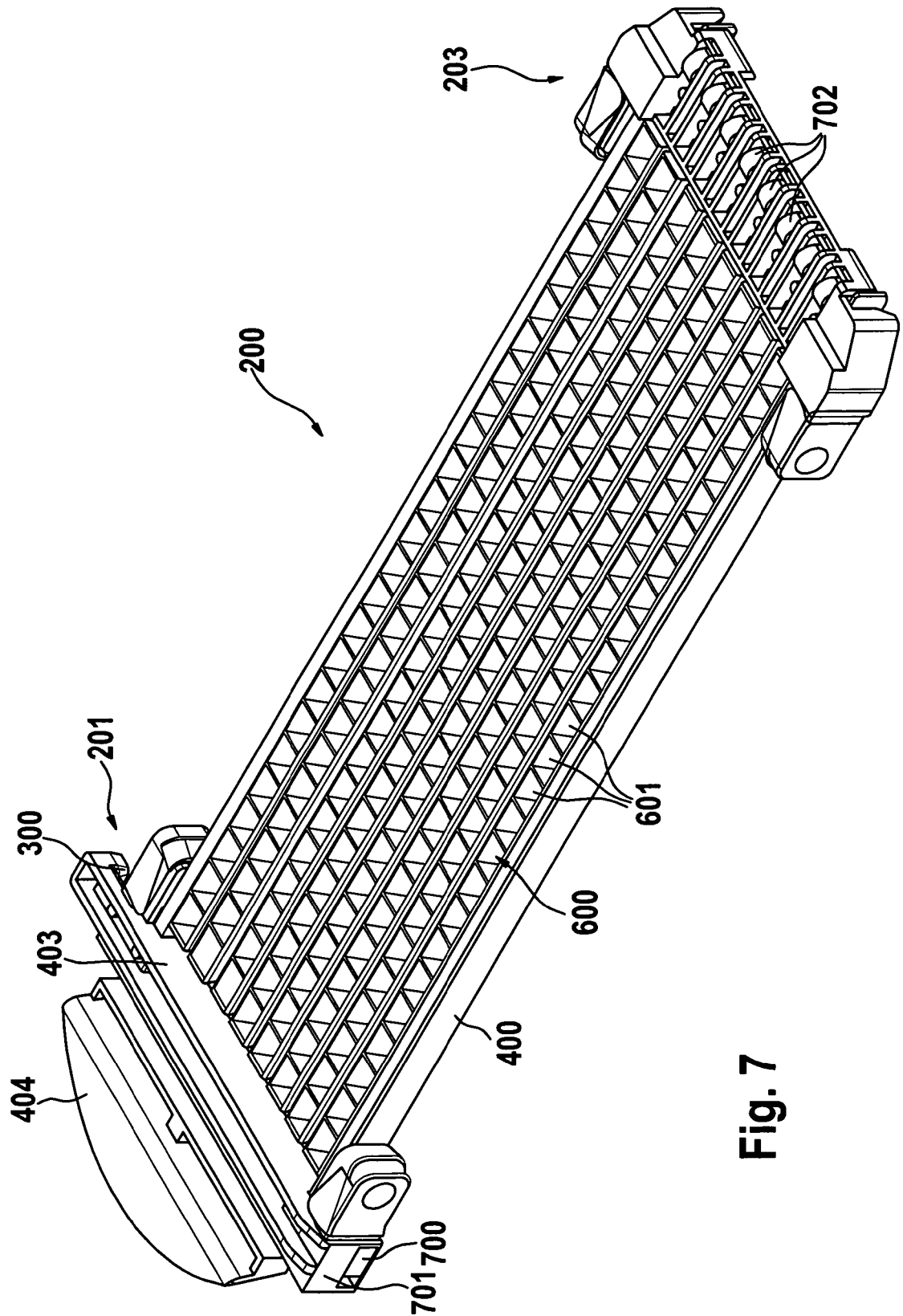
FIG. 7 is a three-dimensional plan view of the insert element of FIG. 4 with compartment frames mounted in all of the gel strips and with electrode members according to an exemplary embodiment of the invention mounted on the insert element.

Referring to FIG. 7, the insert element 200 will be described in a configuration which differs from the configuration of the insert element 200 shown in FIG. 6 in that all gel strip receptions 401 have received a particular one of the compartment frames 600.

Thus, in the configuration of FIG. 7, in each measurement channel 401, an off-gel electrophoresis analysis may be performed. In contrast to this, according to FIG. 6, the measurement channels 401 filled with compartment frames 601 are adapted to perform an off-gel electrophoresis analysis. The remaining measurement channels 401 in which only a gel strip 500, but not a compartment frame 600 is inserted, are adapted to perform an in-gel electrophoresis experiment. Thus, the modular system according to embodiments of the invention may be capable to be flexibly adjusted for a configuration desired by a user, so that the user may perform and combine in-gel and off-gel experiments according to her or his preferences.

In other words, the gel electrophoresis device 100 is adapted to selectively perform a separation of an analyte within the gel strips 500 and/or to perform a separation of an analyte so that the separation products are provided in a solution contained in different cavities 601 of compartment frames 600.

As can be seen in the configuration of FIG. 7, the first electrode member 201 is attached to the insert element 200 to be received in an insert element reception 101 or 102, wherein the first electrode member 201 has electrically contacts which are not shown in FIG. 7 to contact the gel strips 500 received in the gel strip receptions 401.

The second electrode member 203 is attached to the insert element 200 to be received in an insert element 101, 102 to contact the gel strip 500 received in the gel strip reception 401.

Alternatively, it is possible that the first electrode member 201 is attached to the insert element 200 to be received in one of the insert element receptions 101, 102, and that the electrode member 201 directly dips into one of the cavities 601 of the compartment frames 600. According to this configuration, also the second electrode member 203 attached to the insert element 200 to be received in one of the insert element receptions 101, 102 may be directly dipped in a cavity 601 of a compartment frame 600.

According to the embodiment of FIG. 7, the electrode members 201, 203 are clicked onto the top of the insert element 200 loaded with gel strips 500 and compartment frames 600. Thus, the attachment of the electrodes 201, 203 is releasably. Consequently, after use, the compartment frames 600 and/or the gel strips 500 may be removed for cleaning and/or may be substituted by others, and then the electrodes 201, 203 may be clicked again on the insert element 200.

Particularly, the removable attachment of the first electrode member 201 and of the second electrode member 203 to the insert element 200 or to the gel electrophoresis device 100 may be performed by means of a magnetic attachment element. Although this will be described below in more detail, FIG. 7 shows that a permanent magnet 700 is attached at a lateral end portion of a housing 701 of the first electrode member 201.

Referring again to FIG. 2, when the insert element 200 is inserted in the insert element reception 101, the permanent magnet 700 is located close or adjacent to the rail 106. When a ferromagnetic strip is provided at a bottom part of the rail 106, an attracting magnetic force between the permanent magnet 700 and this ferromagnetic strip may be effected so that a secure magnetic locking of the electrode member 201 to the gel electrophoresis device 100 can be realized by means of the magnetic locking element 700 and the corresponding magnet counterpart within the rail 106. In a similar manner, a permanent magnet can also be provided at a lateral part of the housing 701 of the first electrode member 201 adjacent to the electrical contact 300.

As will be described below in more detail, the first electrode member 201 is adapted to concurrently electrically contact each of the gel strips 401 in common. In other words, a common electrical contact between the electrode member 201 and all gel strips below the compartment frames 600 may be effected, wherein this contact can be provided by means of the electrical contact 300 which may be brought in contact to the first electrical contact 107 of the rail 104. Thus, when the first electrode member 201 is slid or shifted along an extension of the gel strips 401, as shown in FIG. 8, a sliding contact is provided between the contact 300 and the strip-like contact 107.

The second electrode member 203 may or may not be adapted to electrically contact each of the gel strips 401 individually. As indicated in FIG. 7, an individual contact to each of the gel strips 401 can be realized by means of individual contact spring elements 702. In other words, the second electrode 203 may be adapted to electrically contact the gel strips 401 individually.

Figure 8:
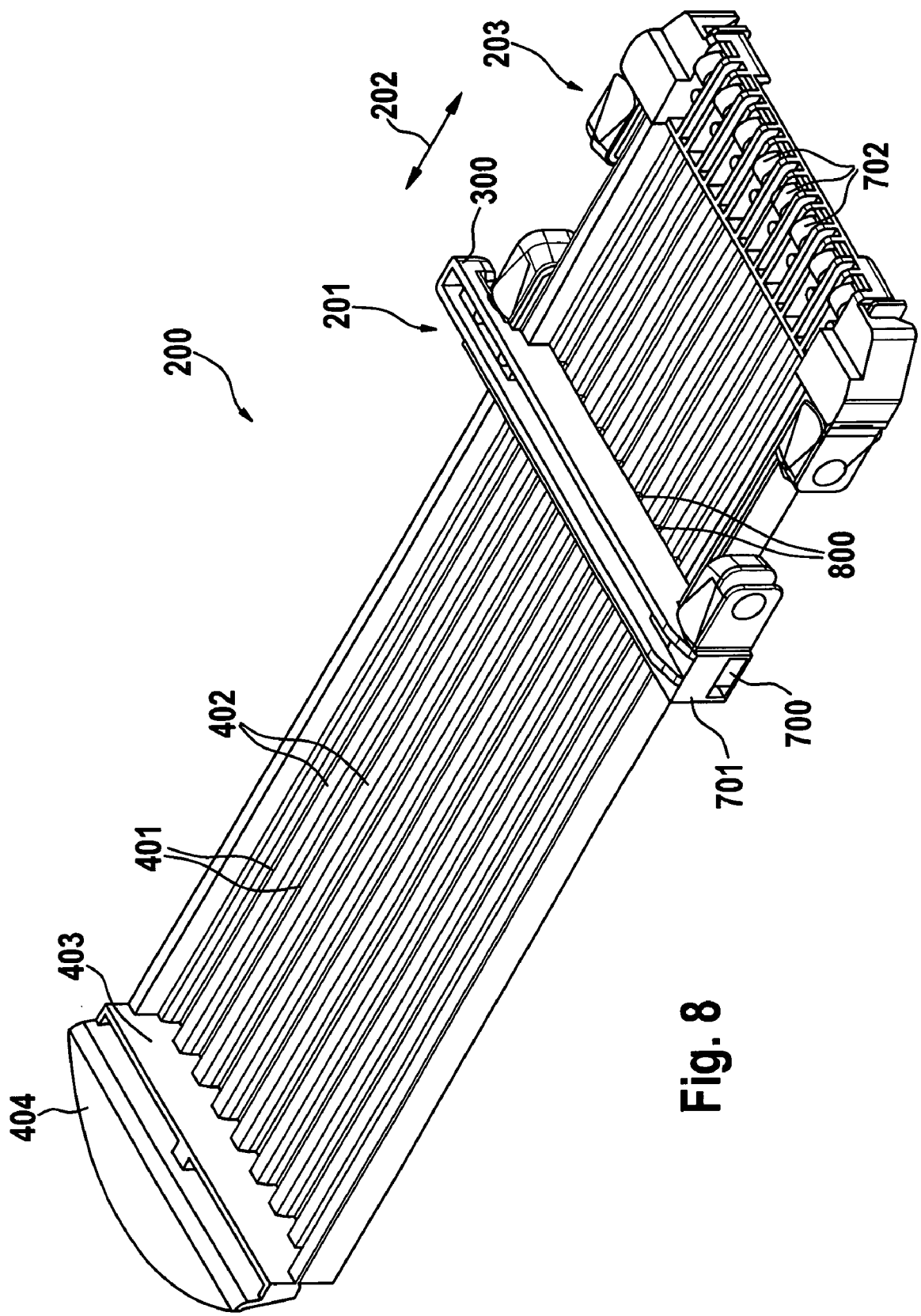
FIG. 8 is a three-dimensional view of the insert element of FIG. 4 without compartment frames and with one of the electrode members shifted along the insert element.

FIG. 8 additionally shows contacts 801 of the first electrode member 201 which contact the various gel strips 500 received in the gel strip receptions 401. However, the contacts 801 are electrically connected to be brought to the same electrical potential, via a connection with the common contact 300.

Figure 9:
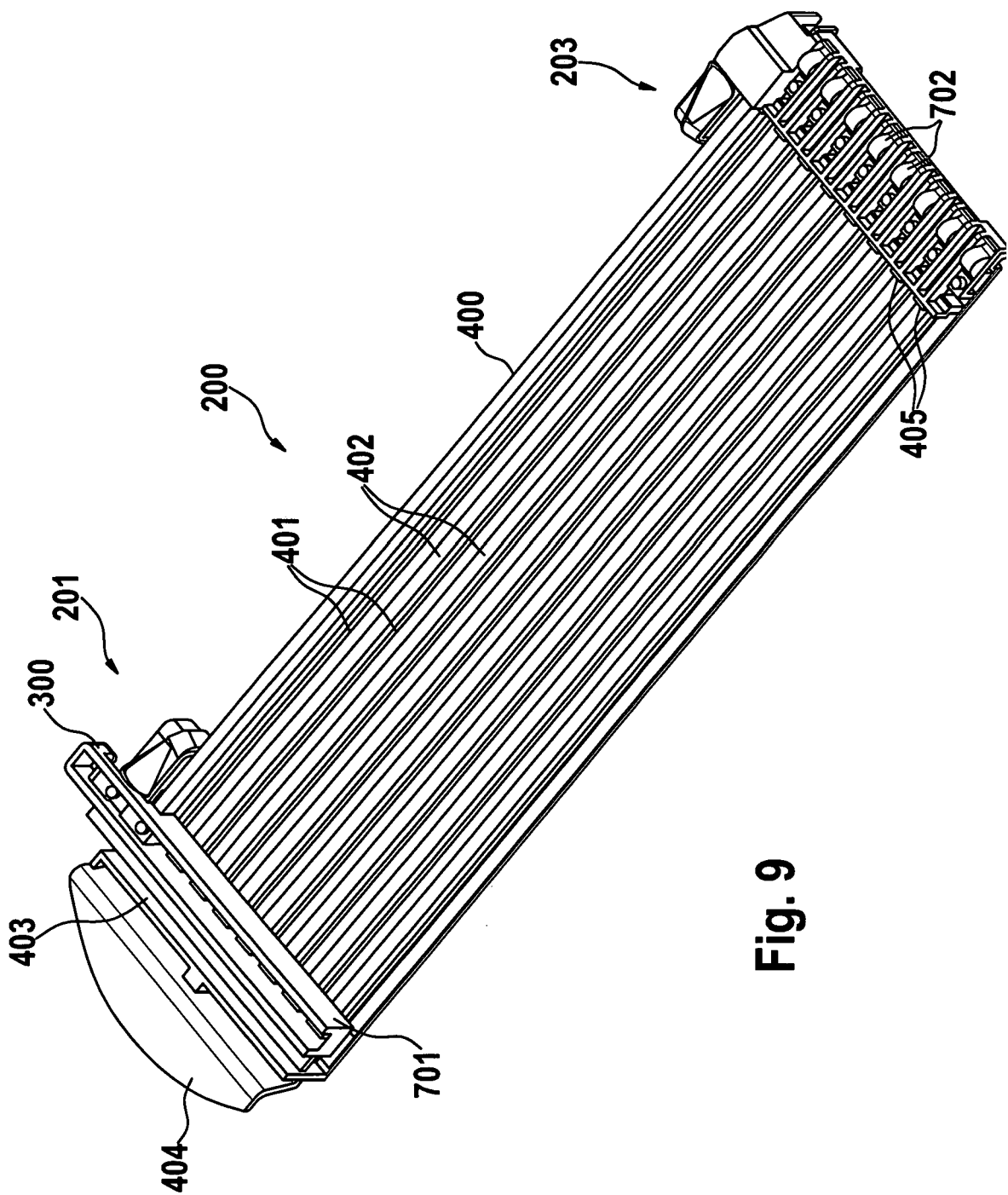
FIG. 9 is a three-dimensional view of the insert element of FIG. 4, wherein some components of the electrode members are removed.

FIG. 9 shows a partially sectional view of the insert element 200 illustrating the geometrical configuration of the different components.

In the following, referring to FIG. 10, details of the electrode arrangement in the insert element 200 will be described in the context of a more detailed description of the second electrode member 203.

The second electrode member 203 is adapted to provide an electrical contact with a plurality of gel strips 500 located in the gel strip receptions 401 individually so that each electrical signal of the gel strips 500 is controllable and/or monitorable separately.

Figure 10:
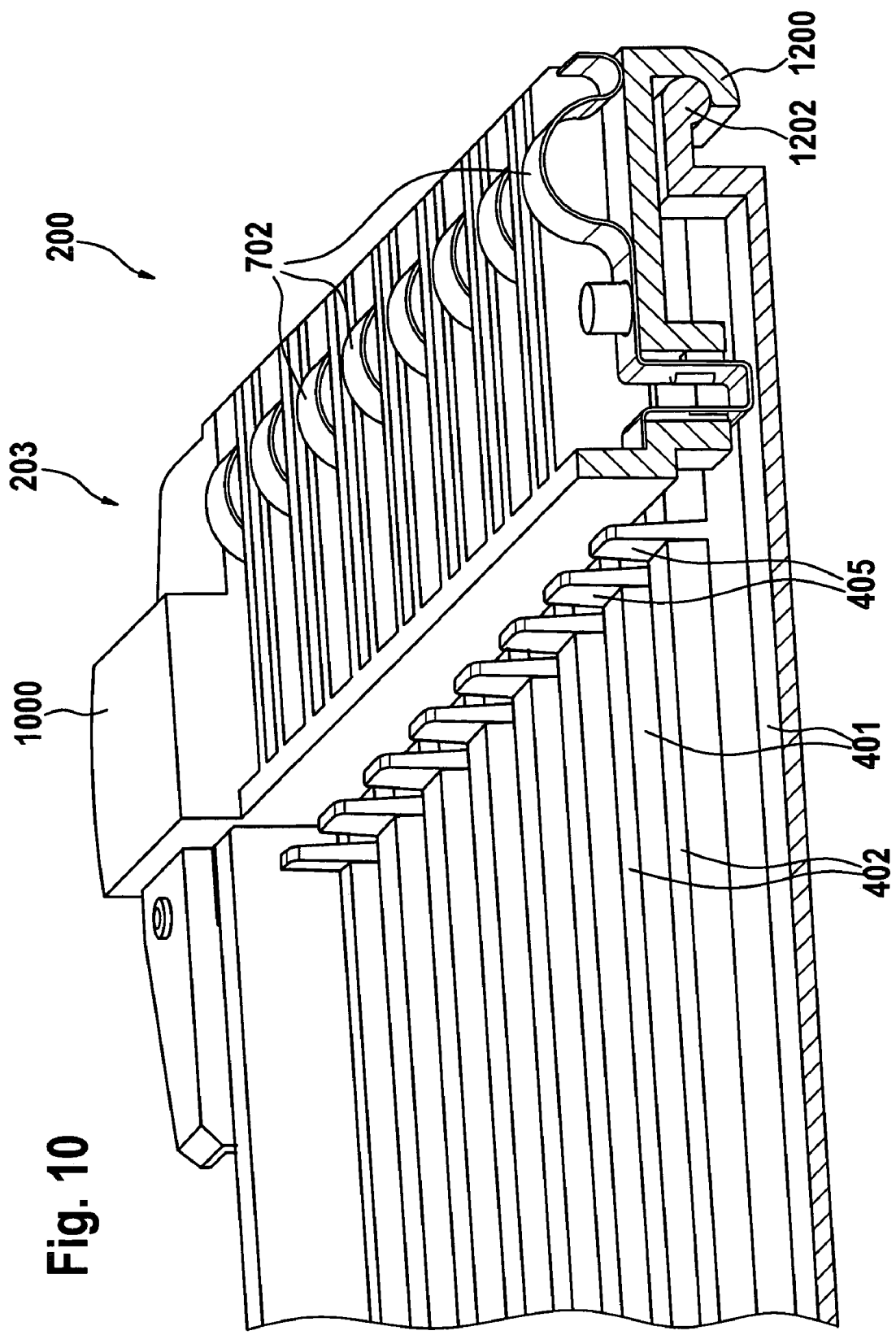
FIG. 10 is a detailed view of a portion of the insert element of FIG. 9 and of one of the electrode members of FIG. 9.

As can be seen in FIG. 10, the second electrode member 203 comprises a second housing 1000 in which the individual electrical contact springs 702 are arranged and are electrically decoupled from one another. Each of the contacts 702 may be connected separately to a circuitry (not shown) in the interior of the gel electrophoresis device 100 for providing control signals and for processing measurement signals detected by the individual contacts 702.

Such a circuit may be provided as an integrated circuit (IC) which may be manufactured in silicon technology or may be conventionally wired. Such a circuit may be mounted on a printed circuit board (PCB).

Although not shown in FIG. 10, the second electrode member 203 may be adapted to provide an electrical contact with at least three gel strips 500 received in gel strip receptions 401, wherein at least two of the at least three gel strips 500 may be combined to a group of gel strips 500. The second electrode member 203 may then be further adapted to provide an electrical contact concurrently with the gel strips 500 combined to a group so that the electrical signals of the gel strips 500 combined to a group are controllable and/or monitorable in common.

In other words, the individual contact functionality of the second electrode member 203 can be further refined in a manner to allow a separate contact of different gel strips 500, however, further allowing to couple different of the contact springs 702 to a group and to control or read out the gel strips 500 within this group in common but separate from gel strips 500 which are not included in this group. It is also possible to provide a switch unit (not shown) within the gel electrophoresis device 100 which flexibly switches or interconnects a plurality of the contacts 702 together, in order to realize a measurement environment in accordance with a user definition.

In the embodiments shown in FIG. 1 to FIG. 10, an electrical control circuit (not shown) can be provided in the gel electrophoresis device 100 and may be coupled to the second electrode member 203 for applying an electrical signal to the gel strips 500 received in the gel strip receptions 401 separately from other gel strips 500 received in other gel strip receptions 401 of the insert element 200.

Furthermore, an electrical monitoring circuit (not shown) may be provided in the gel electrophoresis device 100 and may be coupled to the second electrode member 203 for monitoring an electrical signal of the gel strips 500 received in the gel strip receptions 401 separately from the remaining gel strips 500 received in other gel strip receptions 401.

By means of the electrical monitoring circuit, an operation state of the gel electrophoresis device 100 may be monitored, or an operation state of the gel electrophoresis device 100 may be controlled or regulated based on electrical signals monitored by the electrical monitoring circuit.

For instance, this may include detecting a dehydration (that is to say a loss of humidity) of at least one of the gel strips 500 received in the gel strip receptions 401, rehydrating (that is to say to deliver fluid to) at least one of the gel strips 500 received in one of the gel strip receptions 401, detecting a short circuit in the gel strips 500 received in the gel strip receptions 401 (for instance by detecting that an electric current in the gel strip 500 has exceeded a threshold value), detecting a number of gel strips 500 received in the gel strip receptions 401 being present in the gel electrophoresis device 100 (for instance by detecting the number of gel strips 500 in which an electric current is flowing), detecting at least one measurement parameter (for instance an electrical current, an electrical voltage or an electrical field as a basis for regulating the experimental conditions), diagnosing an error in the gel electrophoresis device 100 (for instance by detecting that an electric current in the gel strip 500 has fallen below a threshold value), adjusting at least one buffer concentration in the gel electrophoresis device (for instance in case that it is detected that the current flowing through one of the gel strips 500 is too high as a consequence of a too high salt concentration in a buffer), or terminating a measurement in the gel strips 500 of the gel electrophoresis device 100 (for instance based on a current or voltage pattern of one of the gel strips 500 which indicates that the electrophoresis process in the gel strip is already finished).

In the following, referring to FIG. 11, a detailed view and a cross section through a part of the insert element 200 is explained.

Figure 11:
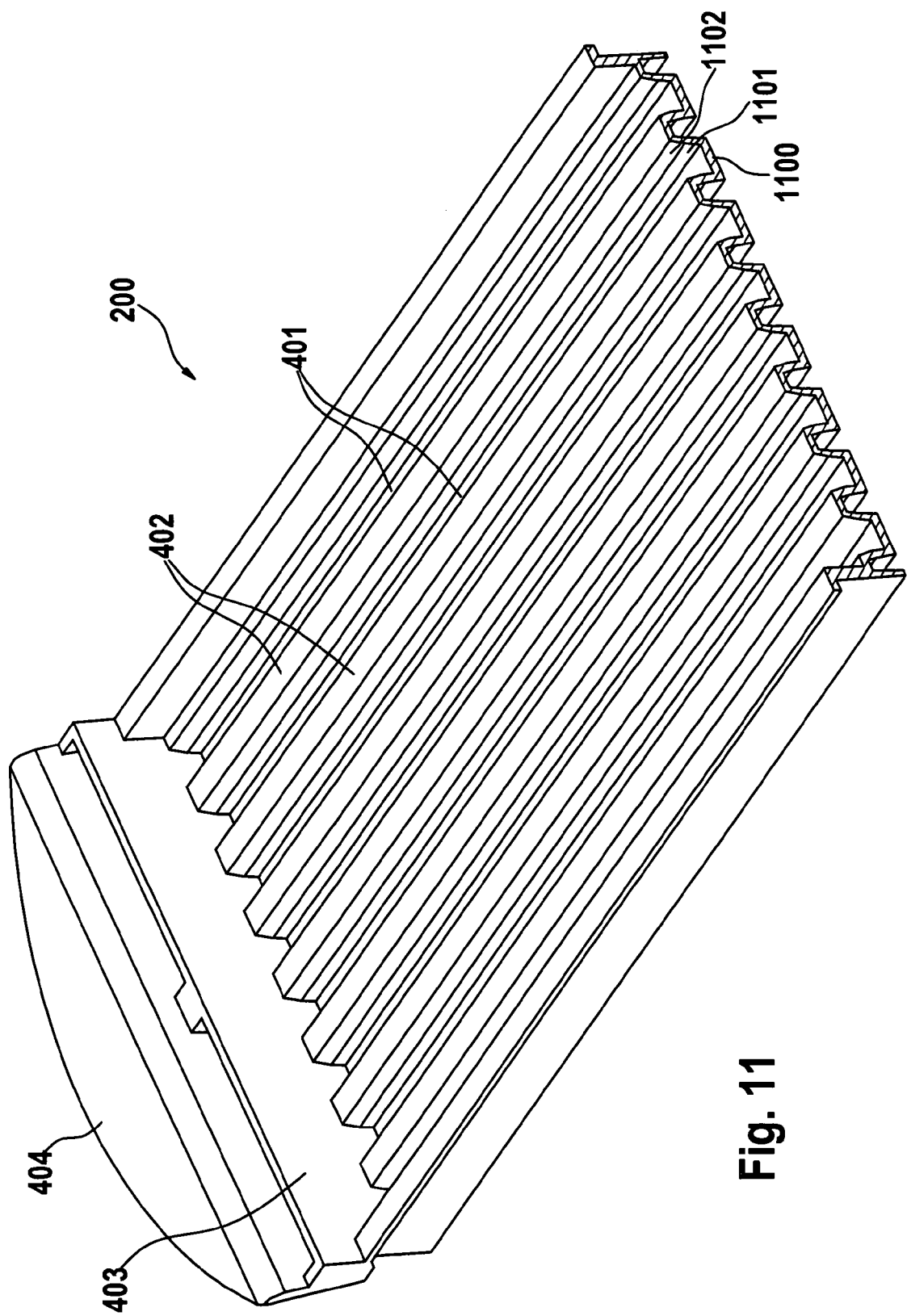
FIG. 11 is a detailed view of a portion of the insert element of FIG. 4.

FIG. 11 shows in more detail the geometric configuration of the gel strip receptions 401 and of the ribs 402. A bottom portion of each of the gel strip receptions 401 comprises a thin-walled bottom plate 1100. Adjacent to the horizontal bottom plate 1100, essentially vertical wall portions 1101 are provided which define, together with the bottom plate 1100, a portion for receiving the gel strips 500. Above the vertical wall portions 1101, an outwardly tapered slant wall part 1102 is provided which supports the reception of the compartment frame 600.

FIG. 12 shows again a detailed view of the second electrode 203 detached from the insert element 200 which is shown from a bottom side in FIG. 12.

Figure 12:
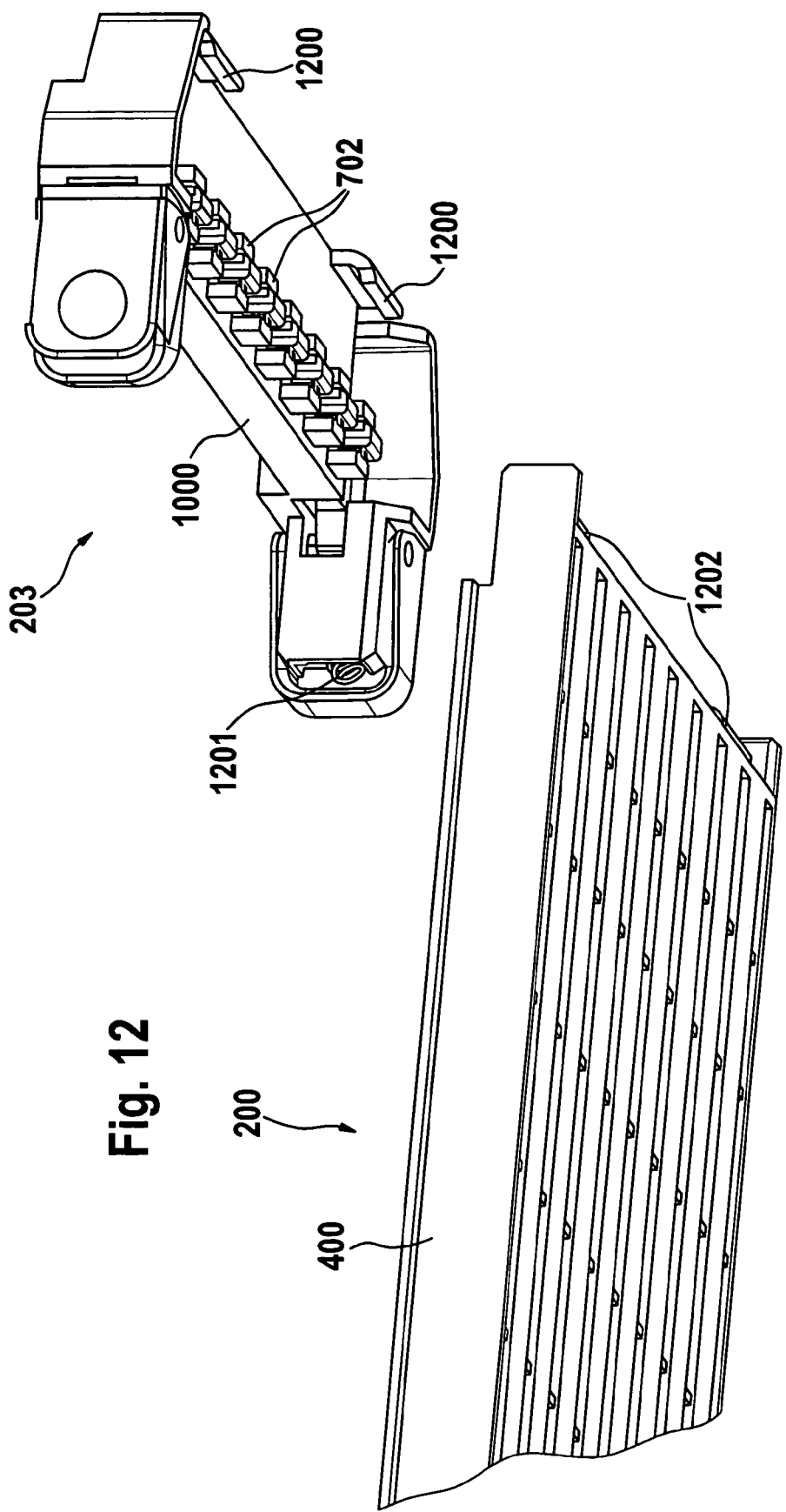
FIG. 12 is a detailed view of a bottom of the insert element of FIG. 4 and of one of the electrode members of FIG. 9.

As can be seen in FIG. 12, springs 1201 are provided in lateral portions of the essentially U-shaped second electrode member 203 to be engaged and fastened to lateral portions of the carrier element 400, that is to say to its side walls.

Further, hook-like elements 1200 are provided at a bottom portion of the second electrode member 203 to be engaged by correspondingly shaped fastening elements 1202 provided at a bottom part of the insert element 200.

Figure 13:
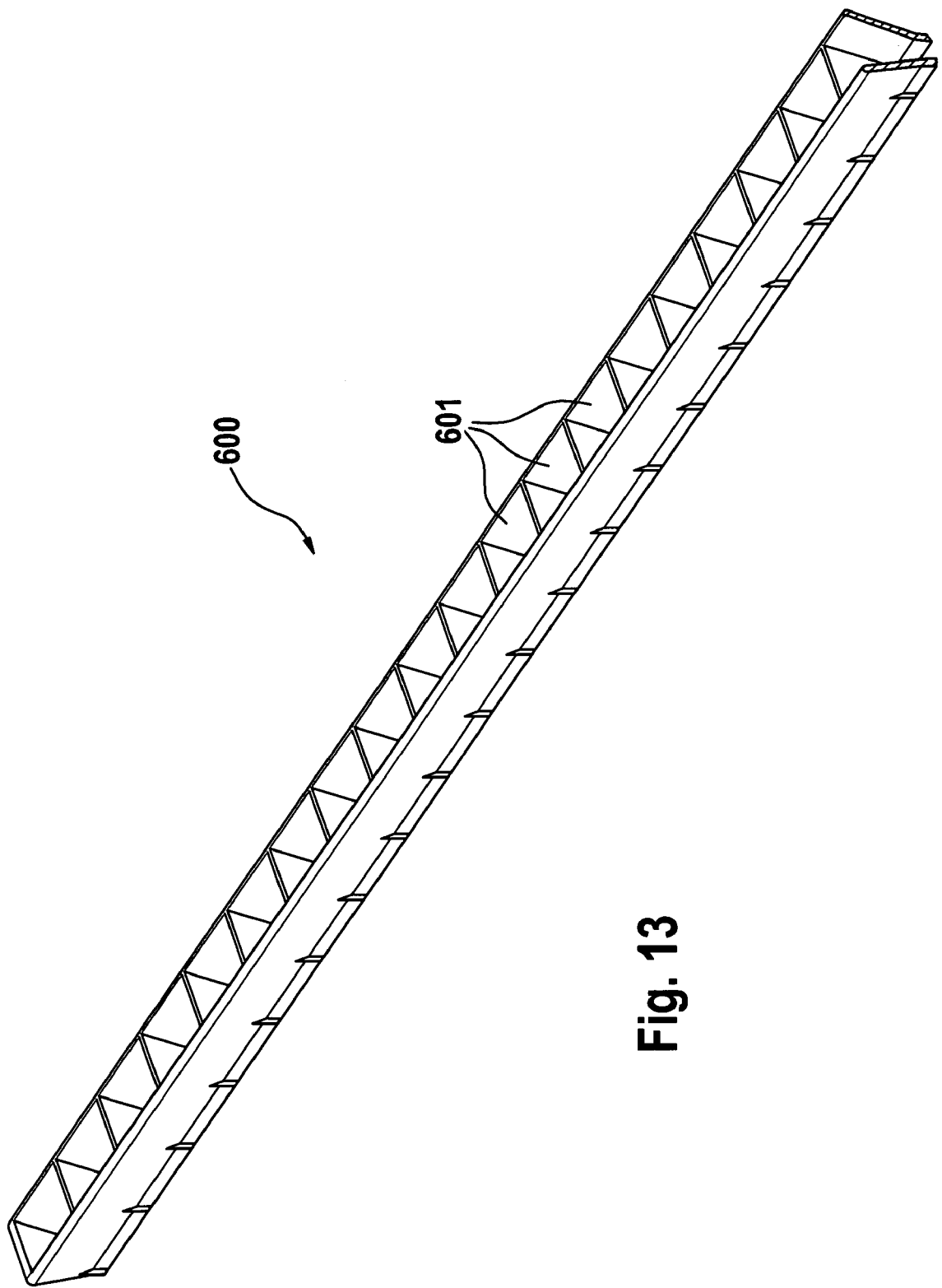
FIG. 13 is a three-dimensional view of a compartment frame having a plurality of cavities according to an exemplary embodiment of the invention.

FIG. 13 shows a detailed view of a compartment frame 600 comprising the plurality of cavity 601.

As can be seen on the right hand side of FIG. 13, the cavities 601 are open at a bottom side to allow a direct fluid contact between a gel strip 500 provided below the compartment frame 600 and fluid filled in one of the cavities 601. Furthermore, the side walls of the cavity 601 are tapered inwardly, so as to be engageable with the correspondingly shaped gel strip receptions 401 of the insert element 200, as can be seen in FIG. 11.

In the following, referring to FIG. 14, the configuration of the first electrode member 201 will be described in more detail.

As already mentioned above, the first electrode member 201 is provided in a housing 701 and has, at a lateral position thereof, a permanent magnet 700 as a magnet locking element for locking the first electrode member 201 to a ferromagnetic stripe provided at a bottom part of one of the rails 104, 106 of the gel electrophoresis device 100.

At a lateral portion of the housing 701, an electrical contact 301 is provided which may be connected to the electrical contact 107 on the rail 104 or to the electrical contact 108 on the rail 106. The first electrode 201 can be clicked on the insert element 200 or tray which can be supported by means of a fastening spring-fit 1401 which may be provided at one or both lateral portions of the first electrode member 201.

When, in this configuration, the first electrode member 201 attached to the insert element 200 is attached to the gel electrophoresis device 100, a magnetic locking between the magnetic element 700 and the ferromagnetic s trip c an b e induced.

Figure 14:
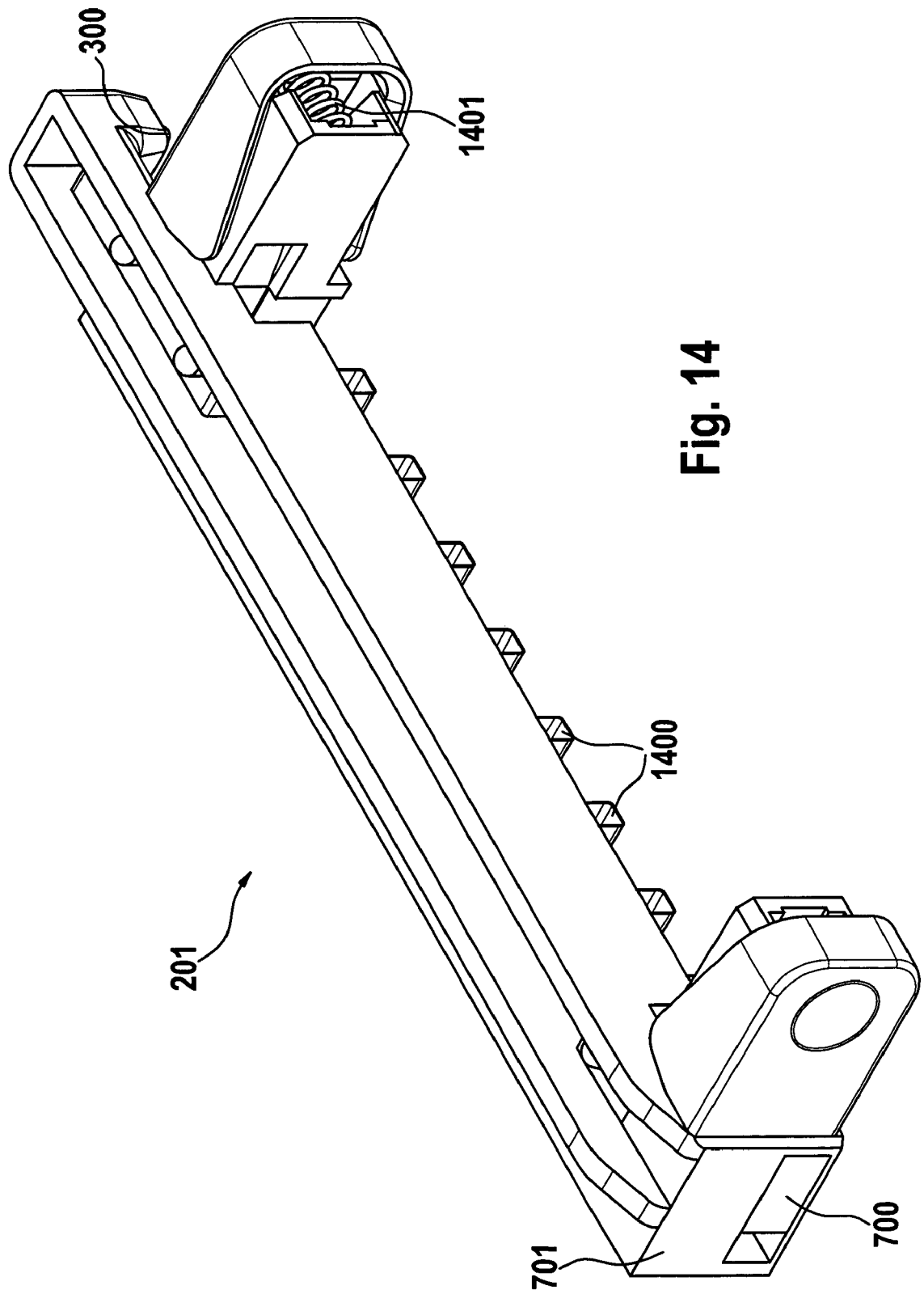
FIG. 14 is a three-dimensional view of an electrode member according to an exemplary embodiment of the invention.

As can further be taken from FIG. 14, the first electrode member 201 is adapted to provide an electrical contact with all gel strips 500 concurrently so that the electrical signals of the gel strips 500 are controllable and/or monitorable in common. For this purpose, contacts 1400 are provided at a bottom side of the first electrode member 201 which contacts 1400 are electrically connected with each other and with the contact 300 to be contactable to the strip-like contact 107 or 108 of the rail 104 or of the rail 106. For instance, the contacts 1400, 300, 107 may supply a high voltage signal to the gel strips 500 received in the gel strip receptions 401.

Figure 15:
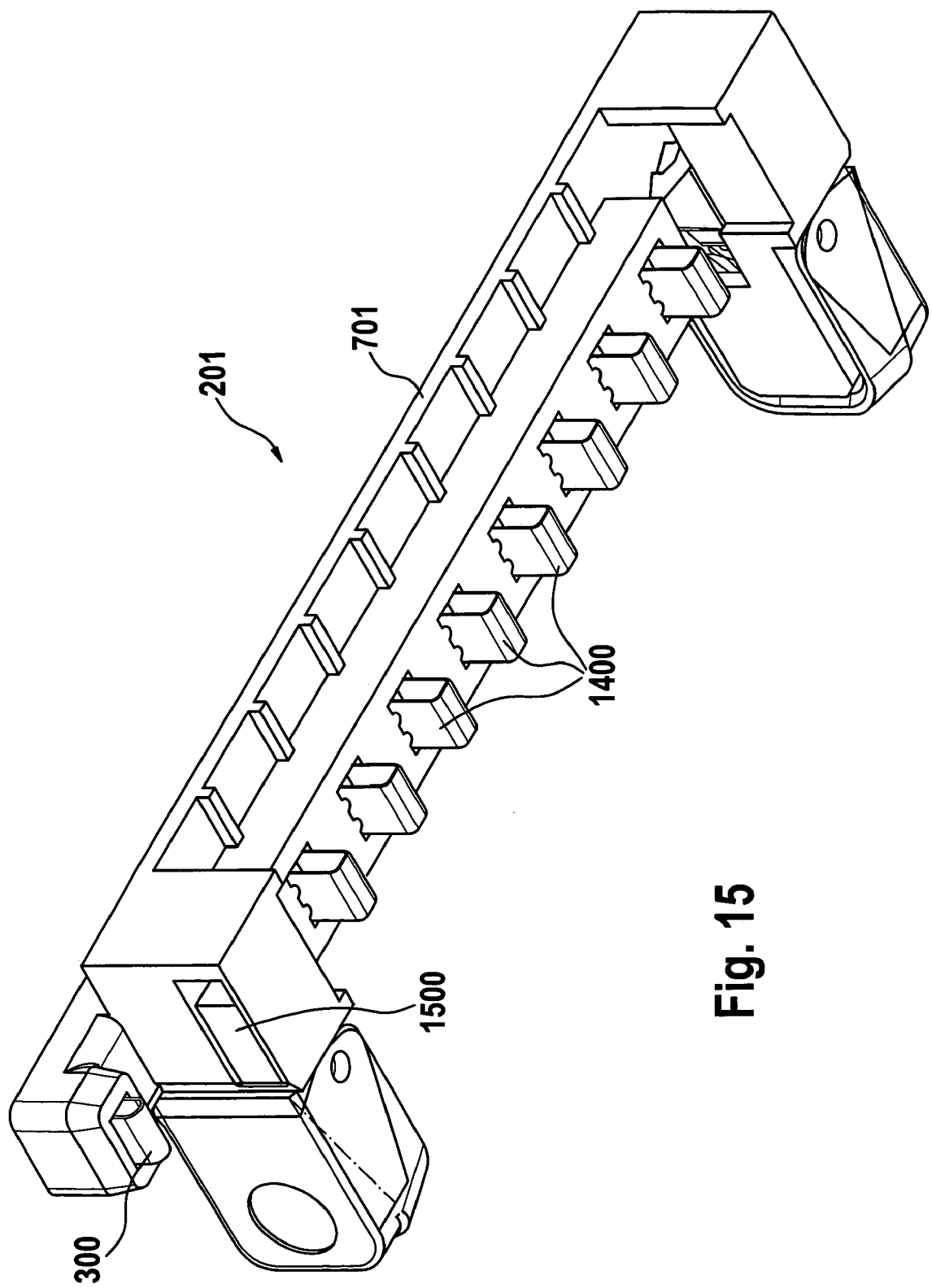
FIG. 15 is a three-dimensional view of an electrode member and of a locking element attached thereto according to an exemplary embodiment of the invention.

FIG. 15 shows a view of the first electrode member 201 so that the common electrical contact 300 can be seen in more detail. Further, it can be seen in FIG. 15 that a lateral position of the first electrode member 201 has attached thereto a permanent magnet 1500 as a magnetic locking element to generate a magnetic locking force together with a ferromagnetic strip provided in the inside of the rail 104 in an operation state in which the first electrode member 201 is attached to the gel electrophoresis device 100.

In the following, referring to FIG. 16, a bottom view of a portion of the gel electrophoresis device 100 and of a part of the insert element 200 will be described.

Figure 16:
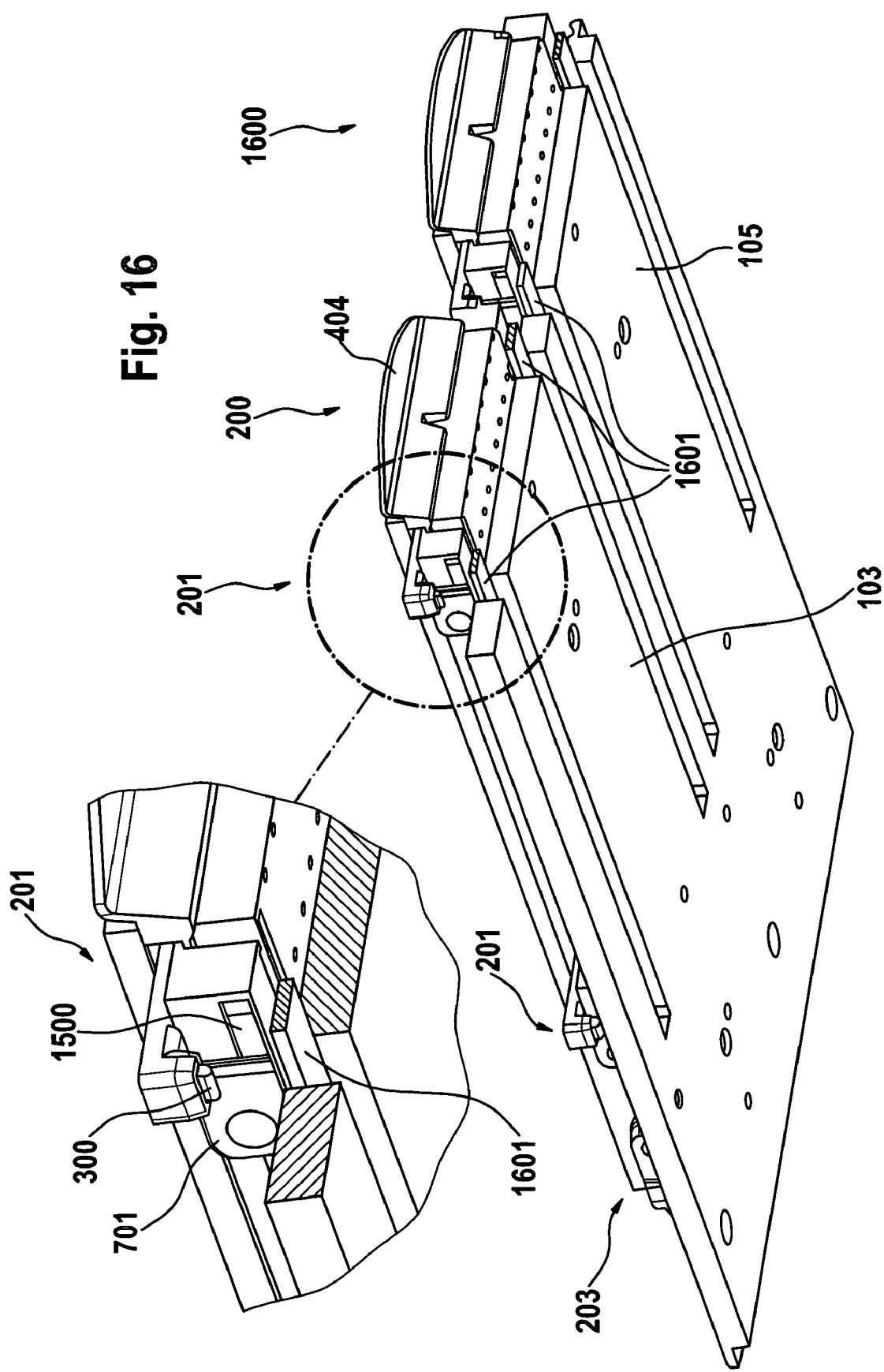
FIG. 16 is a three-dimensional view of a locking element and of a counterpart according to an exemplary embodiment of the invention.

FIG. 16 shows the bottom views of the first platform 103 and of the second platform 105. On the top of the first platform 103, the insert element 200 is inserted. On the top of the platform 105 and thus in the second insert element reception 102, a further insert element 1600 is inserted.

In FIG. 16, the rails 104, 106 are not shown. However, it is shown that at a bottom part of the rails 104, 106, ferromagnetic strips 1601 are provided which extend along an extension direction of the gel strips 500 and which serve as a magnetic counterpart to the permanent magnet 1500 provided at a lateral portion of the first electrode 201 to allow to magnetically lock the electrode 201 to the gel electrophoresis device 100.

In other words, the permanent magnet 1500 and the ferromagnetic strips 1601 form a magnetic locking system comprising the magnetic locking element 1500 connected to the first electrode member 201 to contact the gel strips 500 received in gel strip receptions 401 of the insert element 200, 1600. The ferromagnetic strip 1601 serves as a magnetic counterpart connected to the gel electrophoresis device 100. Thus, the magnetic locking element 1500 is adapted to lock the first electrode member 201 to the gel electrophoresis device 100 by means of the magnetic counterpart 1601.

In other words, the configuration of FIG. 16 illustrates an electrode arrangement for a gel electrophoresis device 100, wherein the first electrode member 201 of the electrode arrangement provides an electrical contact, via the contact 300, with a plurality of gel strips 500. The first electrode member 201 comprises the permanent magnet 1500 as a first locking element to lock the first electrode member 201 to the gel electrophoresis device 100.

The first locking element 1500 is realized as a magnetic locking element, but may alternatively be realized as one of an electric locking element (for instance a ferroelectric material or an electrically conductive material to which an electrical voltage is applied), a vacuum locking element, a mechanical locking element, a snap-in locking element, and a hook and loop fastening locking element. The permanent magnet 1500 locks the first electrode member 201 to the temperature-controllable carrier element 103 of the gel electrophoresis device. It is recalled that the platform 103 may be provided with cooling and/or heating elements, like a heating coil or a Peltier cooling device.

As can be seen in FIG. 16, the permanent magnet 1500 and, see FIG. 7, also the permanent magnet 700, are arranged at lateral portions of the housing 701 of the first electrode member 201. Furthermore, the first electrode member 201 comprises the electrical contact 300 for supplying an electric signal to the first electrode member 201, wherein the electric contact 300 is also provided at a lateral position of the first housing 701.

As can be seen in FIG. 16, the magnetic field generating strip 1601 is provided essentially parallel to the gel strip 500 so that the first electrode member 201 is shiftable along the magnetic field generating strip 1601.

Figure 17:
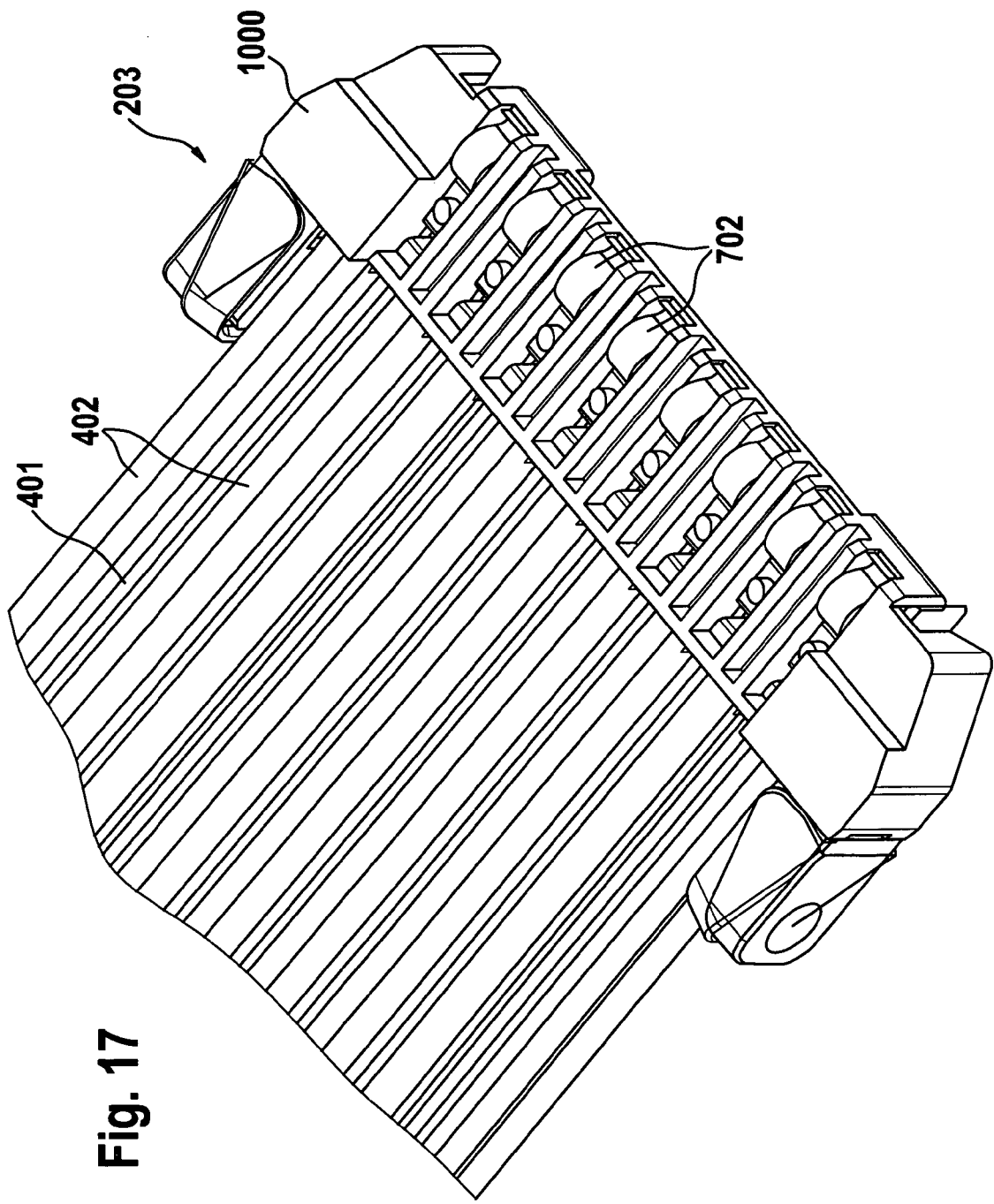
FIG. 17 is a three-dimensional view of the electrode member of FIG. 12.

FIG. 17 shows another view of a second electrode member 203.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

What is claimed is:

1. A gel electrophoresis device, comprising
    a platform adapted to receive a carrier element, wherein the carrier element is adapted to receive one or more gel strips; and
    an electrode arrangement comprising:
    a first electrode member adapted to provide an electrical contact with the one or more gel strips,
        wherein the first electrode member comprises a first locking element adapted to lock the first electrode member to the gel electrophoresis device, and
    the first locking element comprises a magnetic locking element to press the first electrode member by a magnetic coupling onto the platform.

2. The gel electrophoresis device of claim 1, wherein the first locking element is adapted to lock the carrier element to the platform.

3. The gel electrophoresis device of claim 1, wherein the first locking element is adapted to removably lock the first electrode member to the gel electrophoresis device.

4. The gel electrophoresis device of claim 1,
    comprising a second electrode member adapted to provide an electrical contact with the one or more gel strips;
    wherein the second electrode member comprises a second locking element to lock the second electrode member to the gel electrophoresis device.

5. The gel electrophoresis device of claim 1,
    wherein the first locking element comprises at least one of the group consisting of a permanent magnet, an electromagnet, and an electric field generating component.

6. The gel electrophoresis device of claim 1, wherein the first locking element is arranged at a lateral portion of a first housing of the electrode arrangement.

7. The gel electrophoresis device of claim 1, wherein the first electrode member comprises an electric contact for supplying an electric signal to the first electrode member, wherein the electric contact is provided at a lateral portion of a first housing of the electrode arrangement.

8. The gel electrophoresis device of claim 1, comprising
    a counterpart to the first locking element, wherein the counterpart is adapted to lock the first electrode member to the gel electrophoresis device.

9. The gel electrophoresis device of claim 8, wherein:
    the counterpart comprises a magnetic counterpart.

10. The gel electrophoresis device of claim 8, wherein:
    the counterpart comprises at least one of the group consisting of a permanent magnet, an electromagnet and an electric field generating component.

11. The gel electrophoresis device of claim 8, wherein:
    the counterpart comprises one or more electric and/or magnetic field generating strips provided essentially parallel to the one or more gel strips so that the first electrode member is shiftable along the one or more electric and/or magnetic field generating strips.

12. The gel electrophoresis device of claim 1, wherein the gel electrophoresis device is adapted for fluid separation by means of an applied electric field.

13. The gel electrophoresis device of claim 1, wherein the carrier element is temperature-controllable.

14. The gel electrophoresis device of claim 1, wherein the gel electrophoresis device comprises one or more insert element receptions, wherein each of the one or more insert element receptions is adapted to removably receive an insert element forming the carrier element.

15. The gel electrophoresis device of claim 1, wherein the gel electrophoresis device comprises one or more insert element receptions, wherein each of the one or more insert element receptions is adapted to removably receive an insert element forming the carrier element, wherein the first electrode member is removably attachable to the insert element.

16. The gel electrophoresis device of claim 1,
    comprising at least one rail provided essentially parallel to the one or more gel strips so that the first electrode member and/or the second electrode member is or are shiftable along the at least one rail.

17. The gel electrophoresis device of claim 16, wherein the counterpart is arranged along the at least one rail or along a bottom of the at least one rail.

18. The gel electrophoresis device of claim 1, wherein an electric contact for supplying an electric signal to the first electrode member and/or to the second electrode member is arranged along the at least one rail or along a top of the at least one rail.

19. A method of operating a gel electrophoresis device comprising a platform adapted to receive a carrier element, and an electrode arrangement having a first electrode member adapted to provide an electrical contact with one or more gel strips, the method comprising the steps of
    receiving the one or more gel strips in the carrier element; and
    using a first magnetic locking element of the electrode arrangement to lock the first electrode member to the gel electrophoresis device by pressing the first electrode member by a magnetic coupling onto the platform.

20. A gel electrophoresis device, comprising a platform adapted to receive a carrier element, wherein the carrier element is adapted to receive one or more gel strips; and an electrode adapted to provide an electrical contact with the one or more gel strips, and a magnetic element adapted to press the carrier element by a magnetic coupling onto the platform.

* * * * *